United States Patent [19]

Nomura et al.

[11] Patent Number: 5,103,007

[45] Date of Patent: Apr. 7, 1992

[54] LIPIDS

[75] Inventors: Hiroaki Nomura, Ibaraki; Hiroshi Akimoto, Hyogo; Keizo Inoue, Tokyo, all of Japan

[73] Assignee: Takeda Chemical Industries, Ltd., Osaka, Japan

[21] Appl. No.: 427,339

[22] Filed: Oct. 27, 1989

[30] Foreign Application Priority Data

Oct. 27, 1988 [JP] Japan .................................. 63-271685
Mar. 31, 1989 [JP] Japan .................................... 1-81823

[51] Int. Cl.$^5$ .................. C07D 401/12; C07D 401/14;
C07D 403/12; C07D 403/14; C07D 413/12;
C07D 413/14; C07D 417/12; C07D 417/14;
C07D 207/36; C07D 209/32; C07D 211/40;
C07D 213/63; C07D 215/20; C07D 217/24;
C07D 231/18; C07D 233/32; C07D 237/14;
C07D 239/34; C07D 241/18; C07D 249/12;
C07D 251/30; C07D 257/04; C07D 261/12;
C07D 263/18; C07D 271/04; C07D 277/14;
C07D 279/12; C07D 285/02

[52] U.S. Cl. ..................................... 544/316; 548/557;
548/567; 548/569; 548/572; 548/565; 548/348;
548/351; 548/352; 548/353; 548/341; 548/342;
548/379; 548/378; 548/236; 548/187; 548/204;
548/215; 548/156; 548/166; 548/180; 548/507;
548/512; 548/414; 548/415; 548/471; 548/465;
548/466; 548/467; 548/468; 548/472; 548/473;
548/478; 548/499; 548/483; 548/484; 548/485;
548/486; 548/490; 548/491; 548/410; 548/359;
548/371; 548/372; 548/950; 548/573; 548/248;
548/530; 548/531; 548/536; 548/412; 548/413;
548/518; 548/519; 548/532; 548/533; 548/534;
548/535; 548/537; 548/538; 548/541; 548/542;
548/543; 548/544; 548/550; 548/551; 548/336;
548/317; 548/318; 548/319; 548/320; 548/321;
548/337; 548/374; 548/375; 548/376; 548/377;
548/111; 548/112; 548/225; 548/226; 548/227;
548/228; 548/229; 548/230; 548/232; 548/216;
548/243; 548/244; 548/181; 548/117; 548/147;
548/182; 548/183; 548/184; 548/125; 548/119;
548/263.2; 548/263.4; 548/255; 548/118;
548/263.8; 548/264.2; 548/264.4; 548/251;
548/127; 548/130; 548/129; 548/136; 548/138;
548/139; 548/140; 548/141; 548/142; 548/221;
548/217; 548/113; 548/219; 548/159; 548/157;
548/161; 548/163; 548/169; 548/170; 548/171;
544/335; 544/333; 544/224; 544/264; 544/276;
544/277; 544/265; 544/266; 544/267; 544/268;
544/269; 544/270; 544/271; 544/272; 544/244;
544/235; 544/231; 544/237; 544/354; 544/283;
544/284; 544/285; 544/286; 544/287; 544/288

[58] Field of Search ............... 548/557, 572, 348, 353,
548/379, 187, 156, 507, 415, 466, 472, 479, 485,
491, 371, 573, 531, 413, 532, 535, 541, 544, 336,
319, 337, 376, 112, 227, 230, 243, 117, 183, 119,
255, 264.2, 127, 136, 140, 221, 219, 161, 170;
548/567, 565, 351, 341, 378, 204, 166, 512, 471,
467, 473, 483, 486, 410, 372, 248, 536, 518, 533,
537, 542, 550, 317, 320, 374, 377, 225, 228, 232,
244, 147, 184, 263.2, 118, 264.4, 130, 138, 141,
217, 159, 163, 171; 548/569, 352, 342, 236, 215,
180, 414, 465, 468, 478, 484, 490, 359, 950, 530,
412, 519, 534, 538, 543, 551, 318, 321, 375, 111,
226, 229, 216, 181, 182, 125, 263.4, 263.8, 251,
129, 139, 142, 113, 157, 169; 544/335, 264, 266,
270, 235, 283, 287, 291, 258, 386, 385, 362, 366,
370, 382, 84, 113, 121, 127, 131, 135, 140, 157,
161, 168, 172, 176, 58.1, 58.6, 238, 230, 300,
311, 316, 320, 406, 214; 544/333, 276, 267, 271,
231, 284, 288, 292, 259, 337, 359, 363, 367, 371,
80, 85, 116, 122, 128, 132, 137, 141, 158, 162,
169, 173, 177, 58.2, 58.7, 239, 243, 301, 312,
317, 321, 407; 544/224,
544/277, 268, 272, 237, 285, 289, 293, 260, 383,
360, 364, 368, 372, 82, 86, 119, 123, 129, 133,
138, 143, 159, 163, 170, 174, 70, 58.4, 60, 240,
295, 302, 313, 318, 357, 408; 544/399, 265, 269,
244, 254, 286, 290, 257, 399, 384, 361, 365, 369,
373, 83, 87, 120, 124, 130, 134, 139, 144, 160,
164, 171, 175, 57, 58.5, 232, 241, 296, 310, 314,
319, 405, 219; 540/597, 601, 553, 596, 602, 575,
598, 603, 542, 600, 604; 546/242, 147, 153, 241,
172, 155, 341, 174, 156, 342, 18, 157

[56] References Cited

FOREIGN PATENT DOCUMENTS

| | | |
|---|---|---|
| 0094586 | 11/1983 | European Pat. Off. . |
| 0109255 | 5/1984 | European Pat. Off. . |
| 0142333 | 5/1985 | European Pat. Off. . |
| 0238202 | 9/1987 | European Pat. Off. . |
| 0254540 | 1/1988 | European Pat. Off. . |
| 0255366 | 2/1988 | European Pat. Off. . |
| 3521505 | 12/1985 | Fed. Rep. of Germany . |

OTHER PUBLICATIONS

HackH's Chemical Dictionary, 4th Edition, McGraw-Hill Book Co., p. 447 (1969).
Allan Wissner et al., "Analogues of Platelet Activating Factor 3, Replacement of the Phosphate Moiety with a Sulfonylbismethylene Group", J. Med. Chem., vol. 28, pp. 1365-1367 (1985).
Chemical Abstracts, "Peptides for Immune Enhancement", vol. 94, No. 9, Mar. 2, 1981, Abstract No. 66082a, p. 773, col. 2.
Chemical Abstracts, "Thio-Ethylene Glycol Alkyl-(Aryl)Oxymethyl-Substituted Diethers", vol. 103, No. 19, Nov. 11, 1985, Abstract No. 160101g, p. 668, col. 2.

Primary Examiner—John M. Ford
Attorney, Agent, or Firm—Wegner, Cantor, Mueller & Player

[57] ABSTRACT

Lipid derivatives represented by the formula:

(List continued on next page.)

OTHER PUBLICATIONS

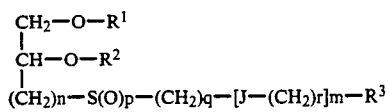

wherein $R^1$ stands for an optionally substituted higher alkyl group, $R^2$ stands for an optionally substituted lower alkyl group or an optionally substituted nitrogen-containing heterocyclic group, $R^3$ stands for a tertiary amino group or a quaternary ammonium group, J stands for oxygen atom or $S(O)t$ (where t deontes 0, 1 or 2), m and n respectively denotes 1 or 2, p denotes 0, 1 or 2, q and r respectively denote an integer of 2 to 5.

and salts thereof have antitumor activities including differentiation-inducing activity and are useful as antitumor agents.

33 Claims, No Drawings

LIPIDS

INDUSTRIAL FIELD OF UTILIZATION

This invention relates to lipids useful as medicines. More specifically, the present invention provides compounds represented by the general formula (I)

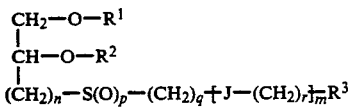

[wherein $R^1$ stands for an optionally substituted higher alkyl group, $R^2$ stands for an optionally substituted lower alkyl group or an optionally substituted nitrogen-containing heterocyclic group, $R^3$ stands for a tertiary amino group or a quaternary ammonium group, J stands for oxygen atom or S(O)t (where t denotes 0, 1 or 2), m and n respectively denote 1 or 2, p denotes 0, 1 or 2, q and r respectively denote an integer of 2 to 5, and J and r may be different in the repetition of m] or pharmaceutically acceptable salts thereof, which are useful as anti-tumor agents.

PRIOR ART

With the recent development of biochemical basic research, differences between tumor cells and normal cells are gradually becoming apparent. Abnormal proliferation, deficiency of contact inhibition, etc. in tumor cells are considered to be due to the structural and functional changes of the cell membrane. On the other hand, certain phospholipids, which are one of the constituents of the cell membrane and serve as a membrane-acting substance, play a role of controlling the activities of functional protein present in the membrane and Produces important and various influences upon cell functions, metabolism and maintenance of life.

From such a background as above, it was disclosed that a phospholipid shown by the following formula (II) would possess anti-tumor action [W. E. Berdel, W. R. E. Bausert, U. Fink, K. Rostetter and P. G. Munder, Anticancer Research 1, 345(1981)]. However, since the compound has a structure resembling closely the platelet activating factor, it has side-effects such as bronchial constriction, platelet aggregation and blood pressure lowering, and these side effects restrict the possibility of clinical use of the compound.

And, as other amphipathic glycerolipids, for example those having no phosphate group represented by the following formula (III) [A=long chain alkyl, B=short chain or long chain alkyl or acyl having 2-5 carbon atoms, D=—$(CH_2)_n$—K, n=1-12, K=an amino group, an acylamino group, a dialkylamino group or a quaternary ammonium group]were disclosed to exhibit antagonism to platelet activating factor (PAF), and to be possibly useful as a therapeutic agent for PAF-related disorders (such as anaphylactic shock). Japanese Unexamined Patent Publication No. 60-100544; Japanese Unexamined Patent Publication No. 58-198445; T. Miyamoto et al., Kyoto Conference on Prostaglandins, Nov. 26-28, 1984, Abst. p.99]. However, no concrete disclosure as to antitumor actions has yet been made.

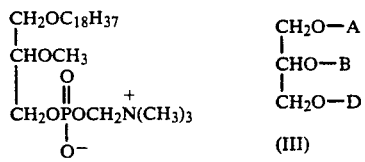

Furthermore, recently, sulfur-containing lipid analogs having no phosphate group, for example, the following compounds (IV) [m=0 or 2] have been disclosed. [A. Wissner et al., J. Med. Chem., 28, 1365 (1985)].

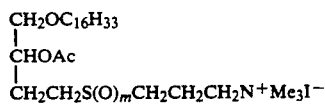

However, the compound (IV) is aimed at PAF antagonistic action and no reference to the anti-tumor actions has yet been made.

PROBLEMS THAT THE INVENTION SOLVES

In the case of drug-therapeutics of cancer, as compared with the therapy of other diseases, there are many difficult problems to be solved, e.g. poor selectivity of available anti-tumor agents, less effectiveness against solid tumors and strong side effects or toxicity. At present, what are especially desired in respect of therapeutic agents of tumors are development of such drugs as set forth below, namely (1) those based on a new reaction mechanism, (2) those having a high selective toxicity to cancer cells and cancer tissues, (3) those effective even against solid tumors and (4) those having less toxicity to patients as far as possible. The present inventors have continued diligent studies for solving these problems, and reached the following solutions.

MEANS OF SOLVING THE PROBLEMS

The present inventors, while taking the above-mentioned problems into consideration, assumed that, among cell-membrane-acting lipids having certain structural factors, there were anti-tumor drugs which have low toxicity against the host and selectively high toxicity against tumor cells, and they have continued diligent research work. There have been reports that tumor cells have, in general, as compared with normal cells, low enzymic activity of splitting ether group. [R. L. Wykle and F. Snyder, The Enzymes of Biological Membranes, A. Martonosi, Ed., Vol. 2, Plenum Press, New York, 1976, p.87; H. J. Lin, F. C. S. Ho, and C. L. H. Lee, Cancer Res., 38, 946 (1978); M. Modolell, R. Andreesen, W. Pahlke, U. Brugger, and P. C. Munder, Cancer Res., 39, 4681(1979)]. Therefore, compounds having alkyl ether structure are promptly metabolized in normal cells, whereas they tend to be accumulated due to being slowly metabolized in tumor cells, especially in lesional tissue, and as the result, they are considered to be correlated with antitumor effects excellent in selectivity, i.e. high therapeutic effects. The present inventors have found that an ether-type derivative of glycerol with a nitrogen-containing heterocyclic ring and having one of the ether linkages substituted with a S(O)p bond [p=0–2], that is, the compound represented by the general formula (I), is low in toxicity, exhibits a high activity of inhibiting propagation of various types of tumor cells, and shows excellent anti-tumor effects and the present invention has been completed.

Namely, the present invention provides compounds represented by the above-mentioned general formula (I) and salts thereof.

In the above-mentioned general formula (I), the higher alkyl group represented by $R^1$ includes alkyl groups having 8-20 carbon atoms such as n-decyl, n-undecyl, n-dodecyl, n-tetradecyl, n-hexadecyl, n-octadecyl and n-eicosyl. The said higher alkyl group may have a substituent such as phenyl, naphthyl, cycloalkyl, lower alkyl, vinyl, acetylene, hydroxy, lower alkoxy or halogen. The higher alkyl groups may contain, as a divalent group, a phenyl group, a naphthyl group, a cycloalkyl group, a vinyl group or an ethynyl group. And the methylene moiety other than at the α-position may be substituted with an oxo group. The said cycloalkyl group includes 3- to 8-membered cycloalkyl groups such as cyclopentyl and cyclohexyl. The said lower alkyl group includes alkyl groups having 1-6 carbon atoms, such as methyl, ethyl, propyl and butyl. The said lower alkoxy group includes alkoxy groups having 1-6 carbon atoms, such as methoxy, ethoxy, propoxy and butoxy. The halogen atom as the substituent of the said higher alkyl group includes fluorine, bromine and chlorine: one to seven halogen atoms constitute a preferred substitution. When $R^1$ is a substituted alkyl group, the substituent may be located at any substitutive position on the higher alkyl group. The said substituted higher alkyl group includes 12-phenyldodecyl, 12-cyclopentyltridecyl, 10-cyclohexyldecyl, 12-cyclohexyldodecyl, 2-hydroxyoctadecyl, 2-methoxyoctadecyl, 2-oxooctadecyl, 16,16,16-trifluorohexadecyl, 18,18,18-trifluorooctadecyl, 14,14,15,15, 16,16,16-heptafluorohexadecyl, 16,16,17,17,18,18,18-heptafluorooctadecyl.

The optionally substituted lower alkyl group represented by $R^2$ includes alkyl groups having 1-6 carbon atoms such as methyl, ethyl, propyl, iso-propyl, butyl, sec-butyl, tert-butyl, pentyl and hexyl.

The optionally substituted nitrogen-containing heterocyclic group represented by $R^2$ includes nitrogen-containing 5- or 6-membered heterocyclic groups such as pyrrolyl, imidazolyl, pyrazolyl, oxazolyl, isooxazolyl, thiazolyl, 1,2,3-oxadiazolyl, triazolyl, tetrazolyl, thiadiazolyl, piperidinyl, N-methylpiperazinyl, N-ethylpiperazinyl, morpholinyl, thiomorpholinyl, pyridyl, pyridazinyl, pyrimidinyl, pyrazinyl and triazinyl, or fused bicyclic rings formed by condensation of the 5- or 6-membered cyclic groups, such as benzoxazolyl, benzothiazolyl, isoindolyl, indolyl, indolizinyl, indazolyl, purinyl, quinolyl, isoquinolyl, quinolidinyl, phthalazinyl, quinoxalinyl, quinazolinyl, cinnolinyl and pteridinyl. Also useful are the corresponding partially or completely hydrogenated groups.

The optionally substituted lower alkyl group or the nitrogen-containing heterocyclic group represented by $R^2$ may have 1-3 substituents. These substituents include halogen atoms (e.g. fluorine, bromine, chlorine), lower ($C_1$–$C_6$)alkyl groups (e.g. methyl, ethyl, propyl, butyl, pentyl, hexyl), lower($C_2$–$C_6$)alkenyl groups (e.g. vinyl, allyl, 1-methylvinyl, 2-methylvinyl), lower($C_3$–$C_6$)cycloalkyl groups (e.g. cyclopropyl, cyclobutyl, cyclopentyl, cyclohexyl), lower($C_5$–$C_6$)cycloalkenyl groups (e.g. cyclopentenyl, cyclohexenyl), phenyl-lower($C_1$–$C_6$)alkyl groups (e.g. benzyl, α-methylbenzyl, phenethyl), phenyl groups, lower($C_1$–$C_6$)alkylthio groups, lower($C_1$–$C_6$)alkylsulfinyl groups, phenylsulfinyl groups, lower($C_1$–$C_6$)alkylsulfonyl groups, phenylsulfonyl groups, mercapto groups, sulfino groups, sulfo groups, phosphono groups, sulfamoyl groups, NN-lower($C_1$–$C_6$)alkylsulfamoyl groups, N,N-di-lower(-$C_1$–$C_6$) alkylsulfamoyl groups (e.g. N,N-dimethylsulfamoyl, N,N-diethylsulfamoyl, N,N-dipropylsulfamoyl, N,N-dibutylsulfamoyl), 3- to 6-membered cyclic aminosulfonyl groups (e.g. 1-pyrrolidinylsulfonyl, 1-piperidinylsulfonyl, 1-piperazinylsulfonyl, 1-methylpiperazin-4-ylsulfonyl, morpholinosulfonyl), imino groups, amidino groups, amino groups, N-lower($C_1$–$C_6$)alkylamino groups, an N,N-di-lower ($C_1$–$C_6$)alkylamino groups, 3- to 6-membered cyclic amino groups (e.g. 1-azetidinyl, 1-pyrrolidinyl, 1-piperidinyl, 1-piperazinyl, 1-methylpiperazin-4-yl, morpholino), N,N,N-trilower($C_1$–$C_6$)alkylammonium groups, lower($C_1$–$C_6$) alkanoyl groups, lower($C_1$–$C_6$)alkanoylamino groups, benzamido groups, benzoyl groups, lower($C_1$–$C_6$)alkanoyloxy groups, benzoyloxy groups, lower($C_1$–$C_6$)alkoxy groups, lower($C_2$–$C_7$)alkoxycarbonyl groups, phenoxy groups, phenylthio groups, hydroxy groups, oxo groups, thioxo groups, epoxy groups, hydroxy-lower($C_1$–$C_6$) alkyl groups, amino-lower($C_1$–$C_6$) alkyl groups, N-lower($C_1$–$C_6$)alkylamino-lower($C_1$–$C_6$) alkyl groups, N,N-di-lower($C_1$–$C_6$)alkylamino-lower($C_1$–$C_6$) alkyl groups, 3- to 6-membered cyclic amino-lower(-$C_1$–$C_6$) alkyl groups (e.g. 1-azetidinyl-, 1-pyrrolidinyl-, 1-piperidinyl-, 1-piperazinyl-, 1-methylpiperazin-4-yl- or morpholino-lower($C_1$–$C_6$)alkyl), N,N,N-tri-lower ($C_1$–$C_6$)alkylammonio-lower($C_1$–$C_6$)alkyl groups, carboxyl groups, carboxy-lower($C_1$–$C_6$)alkyl groups, carbamoyl groups, N-lower($C_1$–$C_6$)alkylcarbamoyl groups, N,N-di-lower ($C_1$–$C_6$)alkylcarbamoyl groups (e.g. N,N-dimethylcarbamoyl, N,N-diethylcarbamoyl, N,N-dipropylcarbamoyl, N,N-dibutylcarbamoyl), 3- to 6-membered cyclic aminocarbonyl groups (e.g. 1-azetidinylcarbonyl, 1-pyrrolidinylcarbonyl, 1-piperidinylcarbonyl, 1-piperazinylcarbonyl, 1-methylpiperazin-4-ylcarbonyl, morpholinocarbonyl), cyano groups, trifluoromethyl groups, and ureido groups.

The tertiary amino group represented by $R^3$ includes groups represented by the formula:

[wherein $R^4$ and $R^5$ are independently an optionally substituted lower alkyl group, or $R^4$ and $R^5$, taken together with the adjacent nitrogen atom, form a cyclic amino group] and optionally substituted heterocyclic groups containing a tertiary nitrogen atom.

The quaternary ammonium group represented by $R^3$ includes groups represented by the formula:

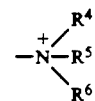

[wherein $R^4$, $R^5$ and $R^6$ are independently an optionally substituted lower alkyl group or they may form, taken together with the adjacent nitrogen atom, a cyclic ammonium group], and optionally substituted heterocyclic groups containing a quaternary nitrogen atom.

The lower alkyl group represented by $R^4$, $R^5$ or $R^6$ includes alkyl groups of 1–6 carbon atoms (e.g. methyl, ethyl, propyl, butyl, pentyl and hexyl), among which a methyl group is preferable.

The cyclic amino group formed by $R^4$ and $R^5$, taken together with the adjacent atom, includes 1-pyrrolyl, 1-pyrazolyl, 1-imidazolyl, piperidino, 1,4-dihydropyridin-1-yl, 1-piperazinyl, 1-[lower($C_1$–$C_6$)alkyl]piperazin-4-yl, morpholino and thiomorpholino group, or they may form a fused bicyclic ring by condensation of 5- or 6-membered ring groups, such as 1-indolyl, 1-indolinyl, 2-isoindolyl or 2-isoindolinyl. And, these groups may be corresponding partially or completely hydrogenated groups.

The heterocyclic ring containing a tertiary nitrogen atom represented by $R^3$ includes a 1-[lower($C_1$–$C_6$)alkyl]-pyrrolidin-(2 or 3)-yl, 1-[lower($C_1$–$C_6$)alkyl]pyrrolin-(2 or 3)-yl, 1-[lower($C_1$–$C_6$)alkyl]pyrrol-(2 or 3)-yl, 1-[lower($C_1$–$C_6$)alkyl]imidazolin-(2 or 4)-yl, 1-[lower(-$C_1$–$C_6$)alkyl]imidazol-(2 or 4)-yl, 1-[lower($C_1$–$C_6$) alkyl]pyrazolin-(3, 4 or 5)-yl, 1-[lower($C_1$–$C_6$)alkyl]-pyrazol-(3, 4 or 5)-yl, oxazol-(2, 4 or 5)-yl, thiazol-(2, 4 or 5)-yl, 1-[lower($C_1$–$C_6$)alkyl]piperidin-(2, 3 or 4)-yl, pyridin-(2, 3 or 4)-yl, pyrimidin-(2, 4, 5 or 6)-yl, pyridazin-(3 or 4)-yl, pyrazin-(2 or 3)-yl, 1-[lower($C_1$–$C_6$) alkyl]piperazin-(2 or 3)-yl, 4-[lower($C_1$–$C_6$)alkyl]morpholin-(2 or 3)-yl, and 4-[lower($C_1$–$C_6$)alkyl]thiomorpholin-(2 or 3)-yl group, or may form a fused bicyclic ring by condensation of 5- or 6-membered ring groups, such as benzoxazol-(2,4,5,6 or 7)-yl, benzothiazol-(2,4,5,6 or 7)-yl, 2-[lower($C_1$–$C_6$)alkyl]isoindolyl, 1-[lower($C_1$–$C_6$)alkyl]indolyl, 7-[lower($C_1$–$C_6$)alkyl]purinyl, isoquinolinyl, quinolinyl, phthalazinyl, quinoxalinyl, quinazolinyl, cinnolinyl or pteridinyl group. And, these groups may be the corresponding partially or completely hydrogenated ones.

The cyclic ammonium group represented by $R^3$, which is formed by $R^4$, $R^5$ and $R^6$, taken together with the adjacent nitrogen atom, may be fused to a bicyclic one, and includes 1-pyridinio, 3-oxazolio, 3-thiazolio, 1-imidazolio, 1-pyrazinio, 1-pyrimidinio, 1-pyridazinio, 4-indolizinio, benzoxazolio, benzothiazolio, 1-quinolinio, 2-isoquinolinio, 2-phthalazinio, 1-naphthylidinio, 1-quinoxalinio, 1- or 3-quinazolinio, 1- or 2-cinnolinio, 1-, 3-, 5- or 8-pteridinio, 1-[lower($C_1$–$C_6$)alkyl]-1-pyrrolinio, 1-[lower ($C_1$–$C_6$)alkyl]-1-pyrrolidinio, 1-[lower(-$C_1$–$C_6$)alkyl]-3-imidazolio, 1-[lower($C_1$–$C_6$)alkyl]-3-imidazolinio, 1-[lower ($C_1$–$C_6$) alkyl]-2-pyrazolio, 1-[lower($C_1$–$C_6$)alkyl]-1-piperidinio, 1-[lower($C_1$–$C_6$)alkyl]-1-piperazinio, 4-[lower($C_1$–$C_6$)alkyl]-4-morpholinio, 4-[lower($C_1$–$C_6$)alkyl]-4-thiomorpholinio, 1-[lower($C_1$–$C_6$) alkyl]-1-indolinio, and 2-[lower($C_1$–$C_6$)alkyl]-2-isoindolinio.

The $R^4$, $R^5$ or $R^6$ in the quaternary ammonium represented by $R^3$ may have, at any substitutive positions, 1-3 substituents, and as the substituents, the substituents described in detail as to the optionally substituted lower alkyl or nitrogen-containing heterocyclic group represented by $R^2$ are suitable.

The heterocyclic group containing a quaternary nitrogen atom represented by $R^3$ may form a fused bicyclic ring, and includes, for example, 1,1-di [lower ($C_1$–$C_6$) alkyl]-pyrrolidinio-(2 or 3)-yl, 1,1-di[lower(-$C_1$–$C_6$)alkyl]pyrrolinio-(2 or 3)-yl, 1,3-di[lower($C_1$–$C_6$-)alkyl]imidazolio-(2, 3 or 4)-yl, 1,3-di[lower($C_1$–$C_6$)alkyl]imidazolinio-(2, 3 or 4)-yl, 3-[lower($C_1$–$C_6$)alkyl]oxazolio-4 or 5)-yl, 3-[lower($C_1$–$C_6$)alkyl]thiazolio-(2, 4 or 5)-yl, 1-[lower($C_1$–$C_6$)alkyl]pyridinio-(2, 3 or 4)-yl, 1,1-di[lower($C_1$–$C_6$)alkyl]piperidinio-(2, 3 or 4)-yl, 1,1-di[-lower($C_1$–$C_6$)alkyl]piperazinio-(2 or 3)-yl, 1-[lower ($C_1$–$C_6$)alkyl]pyrazinio-(2 or 3)-yl, 1-[lower($C_1$–$C_6$)alkyl]pyrimidinio-(2, 4, 5 or 6)-yl, 1-[lower($C_1$–$C_6$)alkyl]-pyridazinio-(3 or 4)-yl, 4,4-di[lower($C_1$–$C_6$)alkyl]morpholinio-(2 or 3)-yl, 4,4-di[lower($C_1$–$C_6$)alkyl]thiomorpholinio-(2 or 3)-yl, 1-[lower($C_1$–$C_6$)alkyl]benzoxazolio-(2, 4, 5, 6 or 7)-yl, 1-[lower($C_1$–$C_6$)alkyl]benzothiazolio-(2, 4, 5, 6 or 7)-yl, 1-[lower($C_1$–$C_6$)alkyl]-quinolinio-(2, 3, 4, 5, 6, 7 or 8)-yl, 2-[lower($C_1$–$C_6$) alkyl]isoquinolinio-(1, 3, 4, 5, 6, 7 or 8)-yl, and 1,1,4-tri[-lower($C_1$–$C_6$)alkyl]piperazinio-(2 or 3)-yl.

These tertiary amino groups or quaternary ammonium groups represented by $R^3$ may further have, at any substitutive positions, 1-3 substituents such as described specifically as to the optionally substituted lower alkyl or nitrogen-containing heterocyclic group represented by $R^2$.

The tertiary amino group or the quaternary ammonium group represented by $R^3$ may optionally form a salt with anion ($W^-$), or may form an internal salt with an anion existing in the molecule. The anion ($W^-$) includes pharmacologically acceptable anions such as those of inorganic acids (e.g. hydrochloric acid, hydrobromic acid, hydriodic acid, boric acid, phosphoric acid, nitric acid, sulfuric acid) or those of organic acids (e.g. acetic acid, lactic acid, tartaric acid, citric acid, methanesulfonic acid, ethanesulfonic acid, benzenesulfonic acid, toluenesulfonic acid). Examples of the anion existing in the molecule include an oxido group ($O^-$ group), a sulfido group ($S^-$ group) and a carboxylato group ($COO^-$ group).

In the general formula (I), J stands for an oxygen atom (—O—) or a group represented by —S(O)t— (wherein t denotes 0, 1 or 2), m and n respectively denote 1 or 2, and p denotes 0, 1 or 2, and q and r respectively denote an integer of 2 to 5. Incidentally, J and r may be different in the repetition of m.

And, the compound (I) has the asymmetric center in the molecule, and its absolute configuration may be S, R or SR(racemic). Therefore, presence of plural diastereoisomers is possible, and these diastereoisomers may, when necessary, be readily separated by means of conventional separation and purification procedures. All of the thus separable diastereoisomers or any mixtures thereof are within the range of the present invention.

The compounds of the present invention can be produced by, for example, the reaction steps as shown below.

In case that n is 1

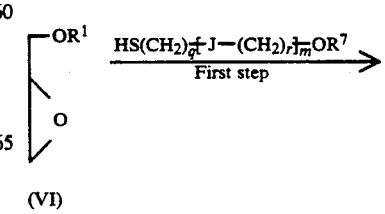

(VI)

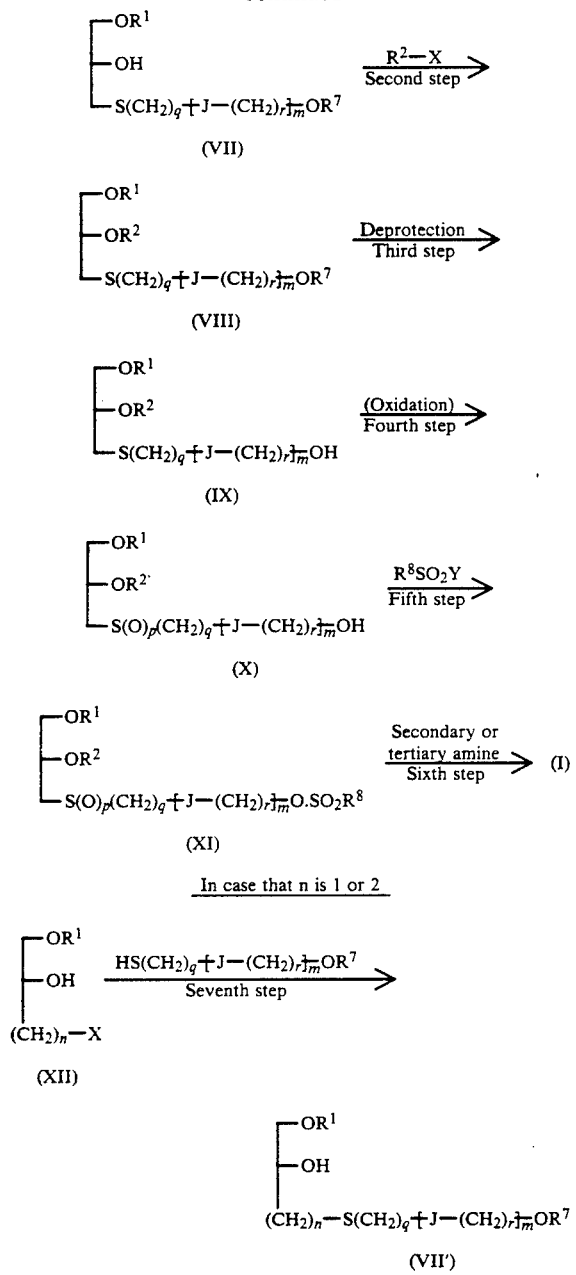

In the above-mentioned steps, $R^1$, $R^2$, $R^3$, $J$, $m$, $n$, $p$, $q$ and $r$ are of the same meaning as defined above, $X$ and $Y$ are respectively an eliminable group, $R^7$ stands for a protecting group of a primary hydroxyl group, and $R^8$ stands for an optionally substituted phenyl, benzyl or lower($C_1$–$C_6$l) alkyl group. Examples of the eliminable groups represented by X and Y include a halogen atom (chlorine, bromine, iodine atom), a methanesulfonyloxy group, a benzenesulfonyloxy group, a p-toluenesulfonyloxy group, a trifluoromethanesulfonyloxy group, and a lower($C_1$–$C_6$) alkanoyloxy group. Examples of the protecting group of primary hydroxyl group, represented by $R^7$, include a trityl group, a benzyl group, a lower($C_1$–$C_6$) alkyl group, a lower($C_1$–$C_6$) alkyloxy-lower($C_1$–$C_6$) alkyl group, a tri-substituted silyl group, a tetrahydrofuranyl group and a tetrahydropyranyl group, each of which may be substituted. Examples of the tri-substituted silyl group include the silyl group substituted with three substituents selected from the group consisting of a lower($C_1$–$C_6$) alkyl group, a phenyl group and a phenyl-lower($C_1$–$C_6$) alkyl group. The groups represented by $R^7$ and $R^8$ may optionally have 1 to 3 substituents. Examples of these substituents include a lower ($C_1$–$C_4$) alkyl group (e.g. methyl, ethyl, propyl, isopropyl, butyl, isobutyl, sec-butyl, tert-butyl), a lower alkoxy group having about 1 to 4 carbon atoms (e.g. methoxy, ethoxy, propoxy, iso-propoxy, n-butoxy, iso-butoxy, sec-butoxy, tert-butoxy), a halogen atom (e.g. fluorine, chlorine, bromine, iodine), a nitro group, a cyano group, a trifluoromethyl group, a di-lower(-$C_1$–$C_4$) alkylamino group (e.g. dimethylamino, diethylamino, dipropylamino, diisopropylamino, dibutylamino), a lower alkylthio group having about 1 to 4 carbon atoms (methylthio, ethylthio, propylthio, isoproylthio, n-butylthio, sec-butylthio, tert-butylthio), a lower alkylsulfinyl group having about 1 to 4 carbon atoms (e.g. methylsulfinyl, ethylsulfinyl, propylsulfinyl, butylsulfinyl), and a lower alkylsulfonyl group having about 1 to 4 carbon atoms (e.g. methylsulfonyl, ethylsulfonyl, propylsulfonyl, butylsulfonyl).

The above-mentioned reaction steps will be specifically described as follows.

The first step:
Starting from alcohol ($R^1OH$), glycidyl ether (VI) is prepared in accordance with a conventional method, which is then allowed to react with HS—$(CH_2)_q[J—(CH_2)_r]_mOR^7$ to give the compound (VII).

The second step:
The compound (VIII) can be prepared by allowing the compound (VII) to react with $R^2$-X of an amount of 1 to 5 equivalents, preferably 1.5 to 3 equivalents, relative to the compound (VII), in the presence of a base in a suitable solvent at $-10°$ to $+100°$ C., preferably $+10°$ to $+50°$ C. for 1 to 100 hours, preferably 4 to 24 hours. Examples of the base to be used for the reaction include metal hydroxides such as sodium hydroxide, potassium hydroxide, lithium hydroxide and barium hydroxide, metal alkoxides such as sodium methoxide, sodium ethoxide and potassium tert-butoxide, metal hydrides such as sodium hydride and potassium hydride, organic metal compounds such as phenyllithium and butyllithium, aliphatic tertiary amines such as triethylamine, and aromatic tertiary amines such as pyridine, α-, β- or γ-picoline, 2,6-lutidine, 4-dimethylaminopyridine, 4-(1-pyrrolidinyl)pyridine, dimethylaniline and diethylaniline. Examples of the reaction solvent include water, alcohols (e.g. tert-butyl alcohol), ethers (e.g. dimethylether, diethylether, tetrahydrofuran, dioxane, monoglyme and diglyme), halogenated hydrocarbons (e.g. dichloromethane, chloroform and carbon tetrachloride), nitriles (e.g. acetonitrile), aliphatic hydrocarbons (e.g. pentane, hexane, heptane and octane), cyclic aliphatic hydrocarbons (e.g. cyclopentane and cyclohexane), aromatic hydrocarbons (e.g. benzene, toluene and xylene), nitromethane, pyridine, dimethylformamide, dimethylsulfoxide, hexamethyl phosphoramide and sulfolane or a suitable mixture thereof. And, when necessary, use of a phase transfer catalyst (e.g. cetyltrimethylammonium chloride) in an amount of 0.01 to 0 2 equivalent, preferably 0.02 to 0.05 equivalent, relative to the compound (VII) serves to allow the reaction to proceed advantageously.

The third step:

The protecting group ($R^7$) of the compound (VIII) can be easily eliminated by a per se known method [J. F. W. McOmie, Protective Groups in Organic Chemistry, Plenum Press, London and New York (1973)] for conversion into the compound (IX).

The fourth step:

The compound (X) can be prepared by allowing the compound (IX) to react with an oxidizing agent of an amount of 0.5 to 1.5 equivalent, preferably 0.8 to 1.2 equivalent, relative to the compound (IX) in a suitable solvent at $-10°$ to $+100°$ C., preferably $0°$ to $+50°$ C., for 10 minutes to 48 hours, preferably for 30 minutes to 24 hours. Preferable oxidizing agents employable for the reaction are peracids (e.g. hydrogen peroxide, peracetic acid, perbenzoic acid, and m-chloro-perbenzoic acid). As the reaction solvent, there can be used water, acetic acid, ketones (e.g. acetone and ethyl methyl ketone), ethers (e.g. dimethyl ether, diethyl ether, dioxane, monoglyme and diglyme), halogenated hydrocarbons (e.g. dichloromethane, chloroform and carbon tetrachloride), aliphatic hydrocarbons (e.g. pentane, hexane, heptane, and octane), cyclic aliphatic hydrocarbons (e.g. cyclopentane and cyclohexane), and aromatic hydrocarbons (e.g. benzene, toluene and xylene) or a suitable mixture thereof. The step of this oxidation reaction may be carried out in advance of any of the second, the third, the fifth or the sixth step. And, when the compound (I) wherein $p=0$ is used, this step is skipped to proceed to the next fifth step directly.

The fifth step:

The compound (XI) can be prepared by allowing the compound (X) to react with a reactive derivative of sulfonic acid ($R^8SO_2$-Y) in an amount of 0.8 to 1.5 equivalent, preferably 0.85 to 1.05 equivalent, relative to the compound (X) in a suitable anhydrous solvent in the presence of a suitable basic catalyst or a deacidifying agent at $-50°$ to $+100°$ C., preferably $-30°$ to $+40°$ C. for 0.5 to 48 hours, preferably 1 to 12 hours. Examples of the anhydrous solvent usable for the reaction include esters (e.g. ethyl acetate), ethers (e.g. dimethyl ether, diethyl ether, tetrahydrofuran, dioxane, monoglyme and diglyme), halogenated hydrocarbons (e.g. dichloromethane, chloroform and carbon tetrachloride), nitriles (e.g. acetonitrile), aliphatic hydrocarbons (e.g. pentane, hexane, heptane and octane), cyclic aliphatic hydrocarbons (e.g. cyclopentane and cyclohexane), aromatic hydrocarbon (e.g. benzene, toluene and xylene), nitromethane, pyridine, dimethylformamide, dimethylsulfoxide, hexamethylphosphoramide and sulfolane or a suitable mixture thereof. Examples of advantageously employable basic catalysts or deacidifying agents include tertiary amines (e.g. aliphatic tertiary amines such as triethylamine; and aromatic tertiary amines such as pyridine, α-, β- or γ-picoline, 2,6-lutidine, 4-dimethylaminopyridine, 4-(1-pyrrolidinyl)pyridine, dimethylaniline and diethylaniline.

The sixth step:

The compound (I) can be prepared by allowing the compound (XI) to react with an excess amount of a secondary or tertiary amine.

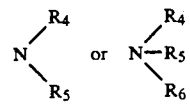

in the absence or presence of a suitable solvent at $-20°$ to $+150°$ C., preferably $0°$ to $+100°$ C. And, if necessary, the reaction can be conducted in a sealed tube at a normal or elevated temperature.

Examples of the solvent employable for the reaction include water, alcohols (e.g. methanol, ethanol, propanol, iso-propanol, butyl alcohol, sec-butyl alcohol, tert-butyl alcohol, ethylene glycol, methoxyethanol and ethoxyethanol), ethers (e.g. dimethyl ether, diethyl ether, tetrahydrofuran, dioxane, monoglyme and diglyme), halogenated hydrocarbons (e.g. dichloromethane, chloroform and carbon tetrachloride), nitriles (e.g. acetonitrile), aliphatic hydrocarbons (e.g. pentane, hexane, heptane and octane), cyclic aliphatic hydrocarbons (e.g. cyclopentane and cyclohexane), aromatic hydrocarbons (e.g. benzene, toluene and xylene), nitromethane, pyridine, dimethylformamide, dimethylsulfoxide, hexamethylphosphoramide and sulfolane or a suitable mixture thereof.

The seventh step:

In the same manner as the first step, the compound (XII) obtained by a per se conventional method and HS-$(CH_2)_q$[J-$(CH_2)_r$]$_m$OR$^7$ are subjected to a per se known reaction to afford the compound (VII). This compound (VII') can be led to the compound (I) in accordance with the second to the sixth steps.

The compound (I) may form a salt with anion ($W^-$), and this anion can be exchanged to a desirable ion by using, for example, an ion-exchange resin.

The compounds(I) can also be prepared by reacting the compound (VI) or (XII) with HS-$(CH_2)_q$-[J-$(CH_2)_r$]$_m$-$R^3$ instead of HS-$(CH_2)_q$-[J-$(CH_2)_r$]$_m$-$OR^7$, and reacting the obtained compound represented by the formula:

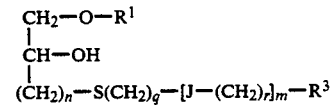

with $R^2$-X in the same manner as that of the second step, and if necessary then subjecting the obtained compound (I) wherein p is 0 to an oxidation reaction in the same manner as that of the fourth step.

The compounds(I) can also be prepared by reacting a compound represented by the formula:

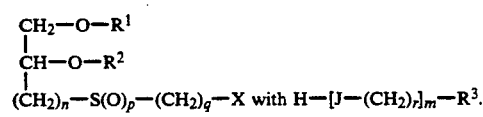

The typical methods of producing the compound (I) are described in the foregoing, but the methods of producing the compound (I) should not be limited to these typical ones.

Operation

The compounds (I) show increased efficacy and prolonged duration with respect to the main actions (e.g.

antitumor activities including differentiation-inducing activity). That is, the compounds prolong the life span of cancer-bearing mice inoculated with ascites-tumor and solid tumor such as murine sarcoma (S180), murine breast cancer (MM 46) and murine colon cancer (colon 26), while remarkably inhibiting the proliferation of human colon adenocarcinoma (colon 205 cells), human nasopharynx cancer (KB cells), human promyelocytic leukemia (HL-60 cells) and human non-small cellular lung cancer (HUT 29 cells and A 549 cells) which are considered to be highly resistant to drugs. And the compounds(I) are found to produce remarkable diminution of side effects (e.g. platelet-aggregating, blood pressure-lowering and vessel permeability-enhancing actions), and no dead mice were found even on intraperitoneal injection of a compound (I) in an amount of 50 mg/kg (body weight). Therefore, the compounds (I) and salts thereof can be administered to cancer-carrying warm-blooded animals as safe antitumor agents. Schedule, route and dosage of administration can be selected according to the subject and symptoms to be treated; the dose for a mammal is usually about 1 to 100 mg/kg (body weight), preferably about 2 to 50 mg/kg (body weight), on the compound (I) basis. Frequency of administration of the compound is about 1 to 3 times a day, or at the intervals of 2 to 7 days. The compounds can also be administered by intravenous drip infusion over a long time in order to maintain the level of the compounds in tissues at a required level over a long period. In parenteral administration of the compound, combination with serum albumin or various globulins is expected to further improve the safety, for example by preventing tissue (local) impairment without affecting the efficacy.

The compounds (I) and the salts thereof are excellent both in hydrophilic and in lipophilic properties, and therefore can be safely administered orally or parenterally to mammals as powders as they are or as a pharmaceutical composition in a suitable dosage form.

Pharmaceutical compositions used for administration contain an effective amount of the compound (I) or a salt thereof and a pharmaceutically acceptable carrier or excipient.

Injections for parenteral administration by this invention include sterilized aqueous or non-aqueous solutions, suspensions, and emulsions. Aqueous solutions and suspensions include distilled water for injection and physiological saline. Non-aqueous solutions and suspensions include Intralipid, propylene glycol, polyethylene glycol, vegetable oils such as olive oil, alcohols such as ethanol, and polysorbate 80. Such compositions may contain further an adjuvant such as an antiseptic, a moistening agent, an emulsifier, or a dispersant, and aqueous injections may contain a supplement such as glucose, serum albumin, or serum (plasma) globulin. These preparations are sterilized by filtration through bacterial filter, by combination of a disinfectant, or by UV irradiation. Sterilized solid preparations are also produced, which are then dissolved in sterilized water or sterilized solvent for injection before use. Tablets and capsules can also be prepared in accordance with routine methods. To prepare these solid compositions, the compound (I) or a salt thereof is mixed with at least one inactive carrier or excipient such as lactose, mannitol, glucose, hydroxypropyl cellulose, microcrystalline cellulose or starch. The compositions may contain an additive other than the inactive carrier or excipient, for example a lubricant such as magnesium stearate or a disintegrator such as calcium cellulose gluconate.

EFFECTS OF THE INVENTION

The effects of the compounds of the present invention are described in detail by the following Test Examples.

TEST EXAMPLE 1

The effect ($IC_{50}$) of the compounds obtained by Examples in inhibiting multiplication of human nasopharynx cancer (KB cells) and human colon adenocarcinoma (colon 205 cells)

Each well of a 96-well microtiter plate was inoculated with 0.1 ml of human nasopharynx cancer (KB cells) ($1 \times 10^4$/ml) or human colon adenocarcinoma (colon 205 cells) ($2 \times 10^4$/ml), which was then subjected to cultivation by allowing to stand at 37° C. for 24 hours in 5% $CO_2$. To the culture was added a 10% MEM solution (manufactured by Nissui Seiyaku or RPMI-1640), and cultivation was continued at 37° C. for 72 hours in 5% $CO_2$. Then, the culture solution was removed with a micro-pipette. To each well was freshly added 0.1 ml of a 10% MEM solution of MTT[3-(4,5-dimethylthiazol-2-yl)-2,5-diphenyltetrazolium bromide](1.0 mg/ml) (Dojin Kagaku). Incubation was conducted at 37° C. for 4 hours, to which was then added 0.1 ml of a 10% SDS (Wako Pure Chemical Industries, Ltd.), and the incubation was continued at 37° C. for 24 hours. Absorbance at a wave length of 590 nm was measured, and the concentration of the drug required for decreasing the cell number of the untreated control group by 50% was decided as the $IC_{50}$ value of the compound. The results are shown in Table 1.

TABLE 1

| Test Compound | KB cells $IC_{50}$ (μg/ml) | Colon 205 cells $IC_{50}$ (μg/ml) |
|---|---|---|
| Compound of Ex. 1 | 1.25 | 1.25 |
| Compound of Ex. 2 | 0.32 | 0.16 |
| Compound of Ex. 3 | 0.16 | 0.63 |
| Compound of Ex. 4 | 0.32 | 0.63 |
| Compound of Ex. 5 | 0.16 | 0.32 |
| Compound of Ex. 6 | 0.32 | 0.63 |
| Compound of Ex. 7 | 0.16 | 0.63 |
| Compound of Ex. 9 | 0.32 | 0.63 |
| Compound of Ex. 13 | 0.63 | 1.25 |
| Compound of Ex. 15 | 1.25 | 1.25 |
| Compound of Ex. 16 | 0.16 | 0.63 |
| Compound of Ex. 17 | 0.32 | 1.25 |
| Compound of Ex. 18 | 1.25 | 1.25 |
| Compound of Ex. 20 | <0.08 | 0.63 |
| Compound of Ex. 21 | 0.32 | — |
| Compound of Ex. 22 | 0.32 | 1.25 |
| Compound of Ex. 23 | 0.63 | 0.63 |
| Compound of Ex. 24 | <0.16 | 0.63 |
| Compound of Ex. 25 | 0.32 | 2.50 |
| Compound of Ex. 26 | 1.25 | 0.63 |
| Compound of Ex. 28 | 1.25 | 5.00 |
| Compound of Ex. 29 | <0.08 | 0.63 |
| Compound of Ex. 30 | 0.16 | 0.32 |
| Compound of Ex. 32 | 0.63 | 1.25 |
| Compound of Ex. 33 | 0.63 | 2.50 |
| Compound of Ex. 34 | 0.32 | 0.63 |
| Compound of Ex. 35 | 0.16 | 0.63 |
| Compound of Ex. 37 | 0.32 | 5.00 |
| Compound of Ex. 38 | 0.63 | 2.50 |
| Compound of Ex. 39 | 0.16 | 0.63 |
| Compound of Ex. 42 | 0.32 | 1.25 |
| Compound of Ex. 43 | 0.32 | 1.25 |
| Compound of Ex. 44 | 0.16 | 0.32 |
| Compound of Ex. 45 | 0.63 | 2.50 |
| Compound of Ex. 46 | 0.32 | 2.50 |
| Compound of Ex. 47 | 0.63 | 1.25 |

TABLE 1-continued

| Test Compound | KB cells IC$_{50}$ (μg/ml) | Colon 205 cells IC$_{50}$ (μg/ml) |
|---|---|---|
| Compound of Ex. 48 | 0.16 | 0.63 |

TEST EXAMPLE 2

Action of the compound in Example against murine colon cancer (colon 26)

Balb/C mice (a group consisting of five mice) were inoculated subcutaneously at dorsolateral area with 2×10⁵ murine colon cancer (colon 26l) cells, and then given intraperitoneally 0.3 mg/mouse of the compound dissolved in physiological saline, eight times, i.e. 1 day, 2 days, 5 days, 6 days, 8 days, 9 days, 12 days and 13 days after the inoculation. After 14 days, the tumor tissue was extirpated and the tumor weight was weighed. Shown in Table 2 is tumor growth inhibition ratio against the untreated control.

TABLE 2

| Test compound | Growth inhibition ratio (1-T/C %) |
|---|---|
| Compound of Example 1 | 48 |

TEST EXAMPLE 3

Action of the compounds obtained in Examples against breast cancer cells MM46

C3H mice (a group consisting of 5 mice) were inoculated intraperitoneally with 1×10⁴ MM46 cells per mouse, and given 0.20 mg/mouse of compounds of Examples dissolved in physiological saline once a day for 4 consecutive days starting from the second day after the inoculation. Shown in Table 3 are the life-span prolongation ratio against the control group without treatment and the number of surviving mice on the 60th day after starting the test.

TABLE 3

| Test Compound | Life-span prolongation ratio (T/C %)* | No. of survivors/ No. of mice tested |
|---|---|---|
| Compound of Ex. 1 | 147 | 4/5 |
| Compound of Ex. 2 | 150 | 2/5 |
| Compound of Ex. 19 | 154 | 2/5 |
| Compound of Ex. 21 | 144 | 2/5 |
| Control Group | 100 | 0/5 |

*only related to mice which died

TEST EXAMPLE 4

Antitumor effect of compounds of Examples against Sarcoma 180 cells

ICR mice (a group consisting of 5 mice) were inoculated intraperitoneally with 1×10⁵ Sarcoma 180 cells per mouse. Then, 0.33 mg/mouse of a compound dissolved in physiological saline was intraperitoneally administered three times, i.e. 1 hour, 1 day and 2 days after the inoculation. Shown in Table 4 are the life-span prolongation ratio against the control group without treatment and the number of surviving mice on the 60th day after the initiation of the test.

TABLE 4

| Test Compound | Life-span prolongation ratio (T/C %)* | Number of survivors/number of mice tested |
|---|---|---|
| Compound of Ex. 1 | 235 | 2/5 |
| Compound of Ex. 3 | 223 | 2/5 |
| Compound of Ex. 6 | 213 | 1/5 |
| Compound of Ex. 24 | 195 | 1/5 |

*only related to mice which died

TEST EXAMPLE 5

Acute toxicity of Compounds of Examples

CDF-1 female mice (5-week old: a group of consisting of 5 mice) were given once intraperitoneally 0.2 ml of a physiological saline solution of a compound of Example. The numbers of mice surviving after 7 days are shown in Table 5.

TABLE 5

| Test Compound | Dosage (mg/kg) | No. of dead mice/ No. of mice tested |
|---|---|---|
| Compound of Ex. 1 | 50 | 0/5 |
| Compound of Ex. 2 | 50 | 0/5 |
| Compound of Ex. 9 | 50 | 0/5 |
| Compound of Ex. 11 | 50 | 0/5 |
| Compound of Ex. 12 | 50 | 0/5 |
| Compound of Ex. 24 | 50 | 0/5 |

EXAMPLES

By way of the following Reference Examples and Working Examples, the present invention will be explained in more detail, but these Examples are not intended to limit the scope of the present invention.

REFERENCE EXAMPLE 1

Production of 2-[2-[2-hydroxy-3-(octadecyloxy)-propylthio]ethoxy]ethyl tetrahydropyranyl ether In tetrahydrofuran (160 ml) were dissolved 1,2-epoxy-3-octadecyloxypropane (20.75 g), 2-(2-mercapto-ethoxy)ethyl tetrahydropyranyl ether (17.0 g) and sodium methoxide (28% methanol solution: 15.3 ml), and the solution was stirred overnight at room temperature. The solvent was distilled off, and the residue was subjected to separation using hexane (300 ml) and water (100 ml). The organic layer was collected, dried, and concentrated. The concentrate was purified by means of a silica gel column chromatography [carrier: 350 g, developing solvent; hexane:ethyl acetate:acetone =8:1:0→3:1:1]to obtain the above-titled compound (23.77 g).

IR (KBr): γ 3450, 2925, 2826, 1462, 1198, 1122, 1077, 1036, 986 cm$^{-1}$

NMR (90 MHz. CDCl$_3$): δ 0.86(3H), 1.05–2.17(38H), 2.61–3.00(4H), 3.34–4.17(13H), 4.96(1H).

REFERENCE EXAMPLE 2

Production of 2-[2-[3-octadecyloxy-2-(pyrimidin-2-yloxy)propylthio]ethoxy]ethyl tetrahydropyranyl ether In tetrahydrofuran (130 ml) was dissolved the compound of Reference Example 1. To the solution was added 60% oily sodium hydride, and the mixture was stirred for 15 minutes at room temperature. To the reaction mixture was then added 2-chloropyrimidine (5.7 g), and the mixture was stirred overnight and there was added dimethylsulfoxide (40 ml), followed by stirring at 45° C. for further two hours. To the reaction mixture was added a small volume of water, and then the solvent was distilled off under reduced pressure.

The residue was dissolved in a mixture of ethyl acetate (250 ml) and hexane (100 ml). The solution was washed with water, to which was added hexane (100 ml), and the mixture was washed with saline, dried, and concentrated to dryness under reduced pressure to obtain the above-titled compound (26.74 g).

NMR (90MHz, CDCl$_3$): δ 0.86(3H), 1.03-2.07(38H), 2.67-3.05(4H), 3.23-4.03(12H), 4.94(1H), 5.39(1H), 6.90(1H,t), 8.50(2H,d).

REFERENCE EXAMPLE 3

Production of 2-[2-[3-octadecyloxy-2-(pyrimidin-2-yloxy)propylthio]ethoxy]ethanol In ethanol (150 ml) was dissolved the compound obtained in Reference Example 2 (26.16 g), to which was added p-toluenesulfonic acid monohydrate (261 mg). The mixture was stirred at room temperature for 7.5 hours. The reaction mixture was neutralized with an aqueous solution of potassium carbonate, and the solvent was distilled off under reduced pressure. The residue was dissolved in ethyl acetate (300 ml), and the solution was washed with water, and the washing was subjected to extraction with ethyl acetate. The ethyl acetate layers were combined, dried and concentrated to dryness. The concentrate was purified by means of a silica gel column chromatography [carrier; 350 g, developing solvent; hexane:ethyl acetate=2:1→0:1] to obtain the above-titled compound (8.46 g).

IR (Neat): γ 3380, 2925, 2860, 1580, 1560, 1465, 1420, 1315, 1115. 1040 cm$^{-1}$ NMR (90 MHz, CDCl$_3$): δ 0.87(3H), 1.07-1.83(32H), 2.51(2H), 2.73-3.02(4H), 3.35-3.85(8H), 5.43(1H), 6.91(1H), 8.49(2H,d).

REFERENCE EXAMPLE 4

Production of 2-[2-[3-octadecyloxy-2-(pyrimidin-2-yloxy)propylsulfinyl]ethoxy]ethanol In dichloromethane (100 ml) was dissolved the compound obtained in Reference Example 3 (7.49 g), to which was added dropwise meta-chloroperbenzoic acid (2.95 g) in dichloromethane (55 ml) under ice-cooling. The mixture was then stirred at room temperature for two further hours. The reaction mixture was washed with an aqueous solution of sodium bicarbonate, dried and concentrated to dryness. The concentrate was purified by means of a silica gel column chromatography [carrier; 350 g, developing solvent; ethyl acetate:methanol=1: 0→5:1] to obtain the above-titled compound (7.23 g).

IR (Neat): γ 3400, 2925, 2860, 1578, 1565, 1465, 1422, 1312, 1120, 1035 cm$^{-1}$.

NMR (90 MHz, CDCl$_3$): δ 0.86(3H), 1.07-1.72(32H), 2.92-4.04(14H), 5.63-5.87(1H), 6.94(1H), 8.50(2H).

REFERENCE EXAMPLE 5

Production of 2-[2-[3-octadecyloxy-2-(pyrimidin-2-yl-oxy)propylsulfinyl]ethoxy]ethyl methanesulfonate In dichloromethane (100 ml) was dissolved the compound obtained in REFERENCE EXAMPLE 4 (7.16 g), to which were added, under ice-cooling, triethylamine (2.74 ml) and methanesulfonyl chloride (1.53 ml). The mixture was stirred at room temperature for one hour. To the reaction mixture was added dichloromethane (50 ml), and the mixture was washed with water then with an aqueous solution of sodium bicarbonate. The dichloromethane layer was dried and concentrated to dryness to obtain the above-titled compound (8.17 g).

IR (KBr): γ 3430, 2920, 2860, 1620, 1576, 1463, 1420, 1345, 1170, 1120, 970, 920 cm$^{-1}$.

NMR (90 MHz, CDCl$_3$): δ 0.86(3H), 1.09-1.72(32H), 2.79-4.05(12H), 3.03(3H), 4.27-4.44(2H), 5.67-5.89(1H], 7.00(1H), 8.58(2H).

REFERENCE EXAMPLE 6

Production of 3-[3-[2-hydroxy-3-(octadecyloxy)-propylthio]propoxy]propyl tetrahydropyranyl ether In the same manner as that of Reference Example 1, the above-titled compound (20.3 g) was obtained from 1,2-epoxy-3-octadecyloxypropane (20 g) and 3-(3-mercaptopropoxy)propyl tetrahydropyranyl ether (9.1 g).

IR (Film): γ 3450, 2925, 2852, 1462, 1565, 1195, 1115, 1075, 1030 cm$^{-1}$.

NMR (90 MHz, CDCl$_3$): δ 0.87(3H], 1.15-2.00(42H), 2.50-2.80(4H), 3.30-3.60(10H), 3.67-4.00(3H), 4.56(1H).

REFERENCE EXAMPLE 7

Production of 3-[3-[3-octadecyloxy-2-(pyrimidin-2-yloxy)propylthio]propoxy]propanol In the same manner as that of Reference Example 2, 3-[3-[3-octadecyloxy-2-(pyrimidin-2-yloxy)propylthio]-propyl tetrahydropyranyl ether was obtained from the compound of Reference Example 6 (21.6 g) and 2-chloropyrimidine (6.62 g). The whole amount of this ether was subjected to, in the same manner as that of Reference Example 3, deprotection by the use of an acid to obtain the above-titled compound (16.3 g).

IR (Film): γ 3420, 2935, 2860, 1580, 1560, 1465, 1425, 1318, 1115, 1065 cm$^{-1}$.

NMR (90 MHz CDCl$_3$): δ 0.87(3H), 1.10-1.80(44H), 2.62(2H), 2.87(2H), 3.28-3.73(8H), 3.75(2H), 5.38(1H), 6.89(1H), 8.47(2H) .

REFERENCE EXAMPLE 8

Production of 3-[3-[3-octadecyloxy-2-(pyrimidin-2-yloxy)propylsulfonyl]propoxy]propanol In dichloromethane (80 ml) was dissolved the compound obtained in Reference Example 7 (8.0 g), to which was portionwise added, while stirring under ice-cooling, meta-chloroperbenzoic acid (6.4 g). The mixture was stirred at room temperature for one further hour, and precipitating insoluble materials were filtered off, and then the filtrate was washed with an aqueous solution of sodium bicarbonate, dried and concentrated to dryness. The concentrate was purified by means of a silica gel column chromatography [carrier; 350 g, developing solvent; ethyl acetate:hexane=2:1→ethyl acetate] to obtain the above-titled compound (7.7 g).

IR (KBr): γ 3410, 2925, 2855, 1580, 1470, 1428, 1332, 1315, 1120 cm$^{-1}$.

NMR (90 MHz, CDCl$_3$): δ 0.87(3H), 1.15-2.05(44H), 3.0-3.80 , 8.51(2H).

REFERENCE EXAMPLE 9

Production of 3-[3-[3-octadecyloxy-2-(pyrimidin-2-yloxy)propylsulfonyl]propoxy]propyl methanesulfonate In the same manner as that of Reference Example 5, the above-titled compound (6.14 g) was obtained from the compound of Reference Example 8 (5.5 g) and methanesulfonyl chloride (1.61 g).

IR (KBr): γ 2925, 2855, 1580, 1560, 1470, 1418, 1340, 1315, 1280, 1160, 1130, 980 cm$^{-1}$.

NMR (90 MHz, CDCl$_3$): δ 0.87(3H), 1.10–2.00(44H), 2.98(3H), 3.00–3.80(12H), 4.22(2H), 5.74(1H), 6.97(1H), 8.50(2H).

REFERENCE EXAMPLE 10

Production of 3-[3-[3-octadecyloxy-2-(pyrimidin-2-yloxy)propylsulfinyl]propoxy]propanol In the same manner as that of Reference Example 4, the above-titled compound (5.82 g) was obtained from the compound of Reference Example 7 (6.0 g) and meta-chloroperbenzoic acid (2.21 g).

IR (KBr): γ 3425, 2925, 2852, 1580, 1570, 1465, 1420, 1315, 1210, 1015 cm$^{-1}$.

NMR (90 MHz, CDCl$_3$): δ 0.87(3H), 1.10–2.00(44H), 2.66–2.93(2H), 3.03–3.87(12H), 5.76(1H), 6.94(1H), 8.51(2H).

REFERENCE EXAMPLE 11

Production of 3-[3-[3-octadecyloxy-2-(pyrimidin-2-yloxy)propylsulfinyl]propoxy]propyl methanesulfonate In the same manner as that of Reference Example 5, the above-titled compound (2.3 g) was obtained from the compound of Reference Example 10 (1.93 g) and methanesulfonyl chloride.

IR (KBr): γ 2925, 2852, 1578, 1560, 1470, 1422, 1350, 1340, 1315, 1165, 1120, 1030, 965 cm$^{-1}$.

NMR (90 MHz, CDCl$_3$): δ 0.87(3H), 1.10–2.00(44H), 2.60–2 92(2H), 2.98(3H), 3.00–3.65(8H), 3.78(2H), 4.21(2H), 5.77(1H), 6.98(1H), 8.57(2H).

REFERENCE EXAMPLE 12

Production of 2-[2-[2-hydroxy-3-(octadecyloxy)-propylthio]ethoxy]ethanol

In tetrahydrofuran (50 ml) were dissolved 1,2-epoxy-3-octadecyloxypropane (10.0 g), 2-(2-mercaptoethoxy)ethanol (11.0 g), sodium borohydride (1.0 g) and sodium methoxide (28% methanol solution: 20.0 ml), and then the solution was stirred for 14 hours at room temperature. The solvent was distilled off, and the residue was dissolved in a mixture of hexane and ethyl acetate. The solution was washed with a dilute hydrochloric acid, and the organic layer was collected, dried and concentrated. The concentrate was purified by means of a silica gel column (chromatography [carrier ; 175 g, developing solvent; hexane:ethyl acetate=5:1→1:1] to obtain the above-titled compound (8.0 g).

IR (KBr): γ 3400, 2920, 2850, 1456, 1345, 1115 cm$^{-1}$.

NMR (90 MHz, CDCl$_3$): δ 0.87(3H), 1.25(32H), 2.51(1H), 2.60–2.90(4H), 3.03(1H), 3.36–4.10(11H).

REFERENCE EXAMPLE 13

Production of 2-[2-[3-octadecyloxy-2-(pyrimidin-2-yloxy)propylthio]ethoxy]ethyl trityl ether In dichloromethane (100 ml) were dissolved the compound obtained in Reference Example 12 (8.0 g) and triphenylchloromethane (100 ml). To the solution was added, while stirring under ice-cooling, triethylamine (2.73 ml), and the mixture was stirred at room temperature overnight. The reaction mixture was washed with water and an aqueous solution of sodium bicarbonate, dried and concentrated to dryness to obtain a crude product of 2-[2-[2-hydroxy-3-(octadecyloxy)propylthio]ethoxy]ethyl trityl ether (11.9 g). The whole amount of this product and 2-chloropyrimidine (3.05 g) were dissolved in tetrahydrofuran (100 ml). To the solution was added 60% oily sodium hydride (0.94 g), and the mixture was stirred for two days at room temperature. The solvent was distilled off, and the residue was dissolved in hexane. The solution was washed with water, dried and concentrated to dryness. The concentrate was purified by means of a silica gel column chromatography [carrier; 175 g, developing solvent; hexane:ethyl acetate=10:1→5:1] to obtain the above-titled compound (11.1 g).

IR (KBr): γ 3050, 3020, 2925, 2850, 1572, 1555, 1488, 1415, 1310, 1118, 1085, 700 cm$^{-1}$.

NMR (90 MHz, CDCl$_3$): δ 0.87(3H), 1.25(32H), 2.83(2H), 2.93(2H), 3.21(2H), 3.46(2H), 3.56–3.80(6H), 5.40(1H), 6.84(1H), 7.15–7.56(15H), 8.45(2H).

REFERENCE EXAMPLE 14

Production of 2-[2-[3-octadecyloxy-2-(pyrimidin-2-yloxy)propylsulfonyl]ethoxy]ethanol In dichloromethane (100 ml) was dissolved the compound obtained in Reference Example 13 (11.1 g), to which was added dropwise under ice-cooling a solution of meta-chloroperbenzoic acid (5.60 g). The mixture was then stirred for one hour at room temperature, and the insoluble materials were filtered off. The filtrate was washed with an aqueous solution of sodium bicarbonate, dried and concentrated to dryness to give a crude product of the sulfonate (12 g). The whole amount of the crude product was dissolved in a mixture of dioxane (75 ml) and methanol (30 ml). To the solution was added 2N hydrochloric acid (30 ml), and the mixture was heated for one hour at 70° C. The reaction mixture was neutralized with sodium bicarbonate, and the solvent was distilled off under reduced pressure. The residue was dissolved in a mixture of hexane and ethyl acetate. The solution was washed with water, dried and concentrated. The concentrate was purified by means of a silica gel column chromatography [carrier; 200 g, developing solvent; hexane:ethyl acetate=2:1→0:1] to obtain the above-titled compound (6.81 g).

IR(KBr): γ 3420, 2920, 2850, 1622, 1574, 1460, 1420, 1305, 1115 cm$^{-1}$.

NMR (90 MHz, CDCl$_3$): δ 0.78(3H), 1.25(32H), 3.00–4.21(14H), 5.83(1H), 7.01(1H), 8.56(2H).

REFERENCE EXAMPLE 15

Production of 2-[2-[3-octadecyloxy-2-(pyrimidin-2-yloxy)propylsulfonyl]ethoxy]ethyl methanesulfonate In the same manner as that of Reference Example 5, the above-titled compound (6.4 g) was obtained from the compound of Reference Example 14 (5.8 g) and methanesulfonyl chloride (1.55 g).

IR(KBr): γ 2925, 2852, 1578, 1560, 1470, 1416, 1360, 1162, 1130 cm$^{-1}$.

NMR (90 MHz, CDCl$_3$): δ 0.87(3H), 1.25(32H), 3.06(3H), 3.20–4.10(12H), 4.36(2H), 5.81(1H), 6.99(1H), 8.53(2H).

REFERENCE EXAMPLE 16

Production of 2-[2-[3-octadecyloxy-2-(pyrimidin-2-yloxy)propylthio]ethoxy]ethyl methanesulfonate In the same manner as that of Reference Example 5, the above-titled compound (3.49 g) was obtained from the compound of the Reference Example 3 (3.0 g) and methanesulfonyl chloride (0.66 ml).

NMR (90 MHz, CDCl$_3$): δ 0.87(3H), 1.26(30H), 1.60(2H), 2.67–3.17(4H), 3.04(3H), 3.24–3.85(8H), 4.27–4.44 (2H), 5.40(1H], 6.91(1H), 8.48(2H).

REFERENCE EXAMPLE 17

Production of 2-[2-[3-(12-cyclohexyldodecyloxy)-2-hydroxypropylthio]ethoxy]ethyl tetrahydropyranyl ether In the same manner as that of Reference Example 1, the above-titled compound (3.57 g) was obtained from 1-(12-cyclohexyldodecyloxy)-2,3-epoxypropane (2.60 g) and 2-(2-mercaptoethoxy)ethyl tetrahydropyranyl ether (1.98 g).

IR (Neat): γ 3450, 2925, 2860, 1460, 1445, 1200, 1120, 1075, 1030 cm$^{-1}$.

NMR (90 MHz, CDCl$_3$): δ 1.00–1.80(39H), 2.60–2.90(5H), 3.30–3.97(13H), 4.55(1H).

REFERENCE EXAMPLE 18

Production of 2-[2-[3-(12-cyclohexyldodecyloxy)-2-(pyrimidin-2-yloxy)propylthio]ethoxy]ethanol In the same manner as that of Reference Example 7, the above-titled compound (0.95 g) was obtained from the compound of Reference Example 17 (1.5 g) and 2-chloropyrimidine (0.60 g).

IR (Neat): γ3400, 2925, 2860, 1575, 1560, 1420, 1315, 1120, 1050, 805 cm$^{-1}$.

NMR (90 MHz, CDCl$_3$): δ 1.00–1.85(33H), 2.51(1H), 2.83(1H), 2.95(1H), 3.40–3.78(10H), 5.45(1H), 6.91(1H), 8.50(2H).

REFERENCE EXAMPLE 19

Production of 2-[2-[3-(12-cyclohexyldodecyloxy)-2-(pyrimidin-2-yloxy)propylthio]ethoxy]ethyl methanesulfonate In the same manner as that of Reference Example 5, the above-titled compound (0.78 g) was obtained from the compound of Reference Example 18 (0.68 g) and methanesulfonyl chloride (0.22 g).

IR (Neat) γ 2930, 2830, 1575, 1560, 1420, 1350, 1170, 1120, 920, 805 cm$^{-1}$.

NMR (90 MHz, CDCl$_3$): δ 1.00–1.80(33H), 2.67–3.10(7H), 3.60–3.80(6H), 4.27–4.40(2H), 5.40(1H), 6.93(1H), 8.51(2H).

REFERENCE EXAMPLE 20

Production of 2-[2-[3-(12-cyclohexyldodecyloxy)-2-(pyrimidin-2-yloxy)propylsulfinyl]ethoxy]ethyl methanesulfonate The compound obtained in Reference Example 18 (0.95 g) was dissolved in dichloromethane (10 ml). To the solution was added dropwise for a period of 10 minutes a solution of m-chloroperbenzoic acid (0.41 g) in dichloromethane (4.0 ml), while stirring under ice-cooling. The mixture was stirred for 30 minutes at the same temperature. To the reaction mixture were added an aqueous solution of sodium hydrosulfite (20 ml) and dichloromethane (40 ml). The mixture was shaken sufficiently, and then the organic layer was collected. The organic layer was washed with an aqueous solution of sodium hydrogencarbonate and water, and dried over anhydrous magnesium sulfate, and then the solvent was distilled off under reduced pressure to give 2-[2-[3-(12-cyclohexyldodecyloxy)-2-(pyrimidin-2-yloxy)propylsulfinyl]ethoxy]ethanol. The whole amount of the product was dissolved in dichloromethane (10 ml). To the solution were added, while stirring under ice-cooling, triethylamine (0.36 g) and methanesulfonyl chloride (0.31 g). The reaction mixture was stirred for 30 minutes at the same temperature, then diluted with dichloromethane (40 ml), and then washed with water. The dichloromethane layer was dried over anhydrous magnesium sulfate, and the solvent was distilled off under reduced pressure to obtain the above-titled compound (1.10 g).

IR (Neat): γ 2930, 2850, 1575, 1515, 1420, 1345, 1310, 1170, 1120, 1010, 915, 805 cm$^{-1}$.

NMR (90MHz, CDCl$_3$): δ 1.00–1.90(33H), 2.85–3.53(9H), 3.70–4.00(6H), 4.27–4.40(2H), 5.60–5.90(1H), 6.95(1H), 8.50(2H).

REFERENCE EXAMPLE 21

Production of 2-[2-[3-octadecyloxy-2-[2-(methylthio)pyrimidin-4-yloxy]propylthio]ethoxy]ethanol Through the same synthesis routes as described in Reference Examples 1 to 3, the above-titled compound (1.84 was obtained from octadecyloxy glycidyl ether (1.96 g), -[2-(tetrahydropyranyloxy)ethoxy]ethyl mercaptan (1.80 g) and 4-chloro-2-(methylthio)pyrimidine (0.84 g).

NMR (90MHz, CDCl$_3$): δ 0.87(3H), 1.03–1.77(32H), 2.53(3H), 2.72–3.02(4H), 3.38–3.83(10H), 5.49(1H), 6.40(1H), 8.22(1H).

REFERENCE EXAMPLE 22

Production of 2-[2-[3-octadecyloxy-2-(pyrimidin-4-yloxy)propylthio]ethoxy]ethanol The compound (1.84 g) of Reference Example 21 was dissolved in ethanol (80 ml), to which was added Raney nickel (20 g), and the mixture was stirred at 70° C for one hour. The catalyst was filtered off and washed with warm ethanol The filtrate and the washing were combined and subjected to distillation under reduced pressure to remove the solvent. The residue was dissolved in ethyl acetate (100 ml), and the solution was washed with water, dried over activated charcoal and anhydrous sodium sulfate. The organic layer was collected and concentrated to dryness. The concentrate was purified by means of a silica gel column chromatography [carrier; 20 g, developing solvent; hexane:ethyl acetate::acetone =4:1:1] to obtain the above-titled compound (0.68 g).

NMR (90MHz, CDCl$_3$): δ 0.87(3H), 1.13–1.77(32H), 2.70–3.03(4H), 3.37–3.55(10H), 5.55(1H), 6.73(1H), 8.42(1H), 8.73(1H).

REFERENCE EXAMPLE 23

Production of 2-[2-[3-octadecyloxy-2-(pyrimidin-4-yloxy)propylthio]ethoxy]ethyl methanesulfonate In the same manner as that of Reference Example 5, the above-titled compound (0.73 g) was obtained from the compound of Reference Example 22 (0.68 g) and methanesulfonyl chloride(0.13 ml).

NMR (90MHz, CDCl$_3$): δ 0.87(3H), 1.12–1.76(32H), 3.03(3H), 2.71–3.00(4H), 3.33–3.89(8H), 4.28–4.44(2H), 5.51(1H), 6.74(1H), 8.43(1H), 8.74(1H).

REFERENCE EXAMPLE 24

Production of 2-[2-[3-octadecyloxy-2-(pyrimidin-4-yloxy)propylsulfinyl]ethoxy]ethanol In the same manner as that of Reference Example 4, the above-titled compound (3.06 g) was obtained from the compound of Reference Example 22 (3.5 g) and m-chloro-perbenzoic acid (1.37 g).

NMR (90MHz, CDCl$_3$): δ 0.87(3H), 1.17–1.88(32H), 2.57–4.13(14H), 5.70–6.05(1H), 6.77(1H), 8.45(1H), 8.77(1H).

REFERENCE EXAMPLE 25

Production of 2-[2-[3-octadecyloxy-2-(pyrimidin-4-ylbxy)propylsulfinyl]ethoxy]ethyl methanesulfonate In the same manner as that of Reference Example 5, the above-titled compound (3.06 g) was obtained from the compound of Reference Example 24 (3.0 g) and methanesulfonyl chloride (0.51 g).

NMR (90MHz, CDCl$_3$): δ 0.87(3H), 1.07–1.73(32H), 3.03(3H), 2.77–4.09(12H), 4.28–4.44(2H), 5.67–6.01 (1H), 6.70–6.83(1H), 8.45(1H), 8.74(1H).

REFERENCE EXAMPLE 26

Production of 2-[2-[2-hydroxy-3-(3,7,11,15-tetramethylhexadecyloxy)propylthio]ethoxy]ethyl tetrahydropyranyl ether In the same manner as that of Reference Example 2, the above-titled compound (5.6 g) was obtained from 3,7,11,15-tetramethylhexadecyloxy glycidyl ether (3.54 g) and 2-(2-acetylthioethoxy)ethyl tetrahydropyranyl ether (2.73 g).

IR (Neat): γ 3460, 2960, 2940, 2875, 1465, 1380, 1115, 1075, 1035, 1020, 990 cm$^{-1}$.

NMR (90MHz, CDCl$_3$): δ 0.63–1.90(45H), 2.63–2.97(5H), 3.37–4.07(14H), 4.63(1H).

REFERENCE EXAMPLE 27

Production of 2-[2-[2-(pyrimidin-2-yloxy)-3-{3,7,11,15-tetramethylhexadecyloxy)propylthio]ethoxy]ethanol In the same manner as that of Reference Example 3, the above-titled compound (3.50 g) was obtained from the compound of Reference Example 26 (5.6 g) and 2-chloropyrimidine (1.75 g).

IR (Neat): γ' 3380, 2955, 2925, 2860, 1575, 1560, 1460, 1415, 1310, 1115, 1045 cm$^{-1}$.

NMR (90MHz, CDCl$_3$): δ 0.73–1.73(39H), 2.43(1H), 2.80 (2H), 2.93(2H), 3.43–3.80(10H), 5.47(1H), 6.93(1H), 8.50(2H).

REFERENCE EXAMPLE 28

Production of 2-[2-[2-(pyrimidin-2-yloxy)-3-(3,7,11,15-tetramethylhexadecyloxy)propylthio]ethoxy]ethyl methanesulfonate In the same manner as that of Reference Example 5, the above-titled compound (1.27 g) was obtained from the compound of Reference Example 27 (1.11 g) and methanesulfonyl chloride (0.30 g).

IR (Neat): γ 2960, 2930, 2870, 1575, 1565, 1460, 1420, 1375, 1350, 1330, 1315, 1170, 1120, 1010, 970, 920 cm$^{-1}$.

NMR (90MHz, CDCl$_3$): δ 0.80–1.77(39H), 2.83(2H), 2.90(2H), 3.03(3H) 43–3.80(8H), 4.30–4.40(2H), 5.40(1H), 6.93(1H), 8.50(2H).

REFERENCE EXAMPLE 29

Production of 2-[2-[2-(pyrimidin-2-yloxy)-3-(3,7,11,15-tetramethylhexadecyloxy)propylsulfinyl]ethoxy]ethanol In the same manner as that of Reference Example 4, the above-titled compound (2.48 g) was obtained from the compound of Reference Example 27 (2.42 g) and m-chloroperbenzoic acid (0.96 g).

IR (Neat): γ 3360, 2955, 2925, 2860, 1575, 1565, 1460, 1420, 1375, 1310, 1115, 1035 cm$^{-1}$.

NMR (90MHz, CDCl$_3$): δ 0.77–1.77(39H), 3.03(2H), 3.23–3.97(12H), 5.67–5.87(1H), 6.93(1H), 8.50(2H).

REFERENCE EXAMPLE 30

Production of 2-[2-[2-(pyrimidin-2-yloxy)-3-(3,7,11,15-tetramethylhexadecyloxy)propylsulfinyl]ethoxy]ethyl methanesulfonate In the same manner as that of Reference Example 5, the above-titled compound (2.80 g) was obtained from the compound of Reference Example 29 (2.40 g) and methanesulfonyl chloride (625 mg).

IR (Neat): γ 2960, 2930, 2870, 1575, 1565, 1465, 1425, 1380, 1350, 1330, 1310, 1170, 1110, 1040, 1015, 970, 920, 805 cm$^{-1}$.

NMR (90MHz, CDCl$_3$): δ 0.77–1.83(39H), 2.97–4.00(12H), 3.03(3H), 4.30–4.40(2H), 5.60–5.97(1H), 8.50(2H)

REFERENCE EXAMPLE 31

Production of 5-[5-[3-octadecyloxy-2-(pyrimidin-2-yl-oxy)propylthio]pentyloxy]pentanol Through the same synthesis routes as described in Reference Examples 1–3, the above-titled compound (8.2 g) was obtained from octadecyloxy glycidyl ether (10.8 g), 5-[5-(tetrahydropyranyloxy)pentyloxy]pentyl mercaptan (9.1 g) and 2-chloropyrimidine (4.4 g).

IR (film): γ 3415, 2935, 2860, 1580, 1565, 1465, 1425, 1328, 1118, 1050 cm$^{-1}$.

NMR (90MHz, CDCl$_3$): δ 0.87(3H), 1.10–1.8(44H), 2.62 (2H), 2.87(2H), 3.28–3.73(8H), 3.75(2H), 5.38(1H), 6 89(1H), 8.47(2H).

REFERENCE EXAMPLE 32

Production of 5-[5-[3-octadecyloxy-2-(pyrimidin-2-yl-oxy)- propylsulfinyl]pentyloxy]pentanol In the same manner as that of Reference Example 4, the above-titled compound (2.0 g) was obtained from the compound of Reference Example 31 (2.1 g) and m-chloroperbenzoic acid (0.56 g).

IR (KBr): γ 3425, 2925, 2852, 1580, 1570, 1465, 1420, 1315, 1210, 1015 cm$^{-1}$.

NMR (90 MHz, CDCl$_3$): δ 0.87(3H), 1.10–2.00(44H), 2.66–2.93(2H), 3.03–3.87(12H), 5.76(1H), 6.94(1H), 8.51(2H).

REFERENCE EXAMPLE 33

Production of 5-[5-[3-octadecyloxy-2-(pyrimidin-2-yl-oxy)propylsulfinyl]pentyloxy]pentyl methanesulfonate In the same manner as that of Reference Example 5, the above-titled compound (2.3 g) was obtained from the compound of Reference Example 32 (1.93 g) and methanesulfonyl chloride (0.53 g).

IR (KBr): γ 2925, 2852, 1578, 1560, 1470, 1422, 1350, 1340, 1315, 1165, 1120, 1030, 965 cm$^{-1}$.

NMR (90MHz, CDCl$_3$): δ 0.87(3H), 1.10–2.00(44H), 2.60–2.92(2H), 2.98(3H), 3.00–3.65(8H), 3.78(2H), 4.21(2H), 5.77(1H), 6.98(1H), 8.57(2H).

REFERENCE EXAMPLE 34

Production of 5-[5-[3-octadecyloxy-2-(pyrimidin-2-yl-oxy)propylsulfonyl]pentyloxy]pentanol In the same manner as that of Reference Example 8, the above-titled compound (3.3 g) was obtained from the 5 compound of Reference Example 31 (4.1 g) and m-chloroperbenzoic acid (2.60 g).

IR (KBr): γ 3410, 2925, 2855, 1580, 1470, 1428, 1332, 1315, 1120 cm$^{-1}$.

NMR (90 MHz, CDCl$_3$): δ 0.87(3H), 1.15–2.05(44H), 3.00–3.80(14H), 5.76(1H), 6.97(1H), 8.51(2H).

REFERENCE EXAMPLE 35

Production of 5-[5-[3-octadecyloxy-2-(pyrimidin-2-yl-oxy)propylsulfonyl]pentyloxy]pentyl methanesulfonate In the same manner as that of Reference Example 5, the above-titled compound (3.3 g) was obtained from the compound of Reference Example 34 (3.1 g) and methanesulfonyl chloride (0.82 g).

IR (KBr): γ 2925, 2855, 1580, 1560, 1470, 1418, 1340, 1315, 1280, 1160, 1130, 980 cm$^{-1}$.

NMR (90 MHz, CDCl$_3$): δ 0.87(3H), 1.10–2.00(44H), 2.98(3H), 3.00–3.80(12H), 4.22(2H), 5.74(1H), 6.97(1H), 8.50(2H).

REFERENCE EXAMPLE 36

Production of 2-[2-(2-methoxy-3-octadecyloxypropylthio)ethoxy]ethanol

To a solution of 2-[2-acetylthioethoxy]ethyl tetrahydropyranyl ether (3.1 g) in tetrahydrofuran (10 ml) were added sodium methoxide (28% methanol solution: 2.5 ml) and 2-methoxy-3-octadecyloxypropyl methanesulfonate (4.12 g) dissolved in tetrahydrofuran (40 ml). The mixture was stirred at room temperature for 12 hours, then at 50° C. for 5 hours. The reaction mixture was concentrated, and the concentrate was dissolved in a mixture of hexane-ethyl acetate. The solution was washed with water, and then the solvent was distilled off. The residue was dissolved in methanol (50 ml), to which was added ion-exchange resin (Amberlyst 15: 1.0 g). The mixture was stirred at room temperature for 4 hours. The resin was filtered off, and then the solvent was distilled off. The residue was purified by means of a silica-gel chromatography [carrier ; 150 g, developing solvent; hexane: ethyl acetate =3:1]to obtain the above-titled compound (2.83 g).

IR (film): γ 3450, 2920, 2855, 1462, 1350, 1115 cm$^1$.

NMR (90MHz, CDCl$_3$): δ 0.87(3H), 1.27(32H), 2.76(4H), 3.43(3H), 3.33–3.86(1H).

REFERENCE EXAMPLE 37

Production of 2-[2-[2-[3-octadecyloxy-2-(pyrimidin-2-yl-oxy)propylthio]ethoxy]ethanol Through the same synthesis routes as described in Reference Examples 1 to 3, the above-titled compound (5.5 g) was obtained from octadecyloxy glycidyl ether (5.0 g), 2-[2-[2-acetylthioethoxy]ethoxy]ethyl tetrahydropyranyl ether (5.37 g) and 2-chloropyrimidine (2.06 g).

IR (film): γ 3420, 2925, 2850, 1580, 1560, 1465, 1420, 1310, 1118 cm$^{-1}$.

NMR (90MHZ, CDCl$_3$]: δ 0.87(3H], 1.27(32H), 2.45(1H), 2.82(2H), 2.93(2H), 3.35–3.80(14H), 5.40(1H), 6.92(1H), 8.50(2H).

REFERENCE EXAMPLE 38

Production of 2-[2-[2-[3-octadecyloxy-2-(pyrimidin-2-yloxy)propylsulfinyl]ethoxy]ethoxy]ethanol In the same manner as that of Reference Example 4, the above-titled compound (1.70 g) was obtained from the compound of Reference Example 37 (1.80 g) and m-chloroperbenzoic acid (0.54 g).

IR (KBr): γ 3400, 2920, 2850, 1570, 1470, 1425, 1315, 1120 cm$^{-1}$.

NMR (200MHz, CDCl$_3$): δ 0.88(3H), 1.25(32H), 2.85–3.85(16H), 3.97(2H), 5.78(1H), 6.98(1H), 8.53(2H).

REFERENCE EXAMPLE 39

Production of 3-benzyloxy-4-octadecyloxybutyronitrile

In dimethylsulfoxide (400 ml) was dissolved 2-benzyloxy-3-octadecyloxypropyl methanesulfonate (54.8 g). To the solution was added sodium cyanide (15.31 g), and the mixture was stirred at 50° C. for 16 hours, and then stirred at 60° C. for 1.5 hour. The reaction mixture was poured into water (200 ml), and subjected to extraction with hexane (400 ml). The hexane layer was collected, washed with water, dried, and concentrated to dryness. The residue was purified by means of a silica gel column chromatography [carrier ; 750 g, developing solvent; hexane:ethyl acetate =1:1–4:1] to obtain the above-titled compound (38.75 g).

IR (KBr): γ 2920, 2850, 2240, 1465, 1345, 1110, 730, 690 cm$^{-1}$.

NMR (90MHz, CDCl$_3$): δ 0.87(3H), 1.03–1.77(32H), 2.53–4.73(2H), 3.30–3.71(4H), 3.82(1H), 4.66(2H), 7.33(5H).

REFERENCE EXAMPLE 40

Production of methyl 3-benzyloxy-4-octadecyloxybutyrate

In a mixture of methanol (150 ml) and ether (150 ml) was dissolved the compound of Reference Example 39 (38.68 g). Into the solution was blown hydrogen chloride gas, and then the mixture was allowed to stand for 3 hours at room temperature. To the reaction mixture were added water (300 ml) and ethyl acetate (300 ml), and the mixture was stirred for 40 hours at room temperature. Water (100 ml) was added to the mixture, and the resulting mixture was then subjected to extraction with a mixture of hexane -ethyl acetate and then with dichloromethane. The extracts were combined, washed with water and then concentrated to obtain the above-titled compound (40.15 g).

NMR (90 MHz, CDCl$_3$): δ 0.86(3H), 1.03–1.84(32H), 2.57(2H), 3.30–3.60(4H), 3.65(3H), 4.04(1H), 4.63(2H), 7.33(5H).

REFERENCE EXAMPLE 41

Production of 3-benzyloxy-4-octadecyloxybutanol

In tetrahydrofuran (200 ml) was suspended aluminum lithium hydride (6.64 g). To the suspension was added dropwise, while stirring under ice-cooling, a solution of the compound of Reference Example 40 (42.1 g) in tetrahydrofuran (200 ml). The reaction mixture was stirred at room temperature for 2 hours, and then, while stirring under ice-cooling, a 1N aqueous solution of sodium hydroxide (30 ml). Insoluble materials were removed by filtration with celite, and the filtrate was washed sufficiently with tetrahydrofuran. The filtrate and the washing were combined and concentrated to dryness to obtain the above-titled compound (35.5 g).

NMR (90MHz, CDCl$_3$): δ 0.87(3H), 1.07–1.94(34H), 3.21–3.94(7H), 4.44–4.86(2H), 7.34(5H).

REFERENCE EXAMPLE 42

Production of 3-hydroxy-4-octadecyloxybutanol

In a mixture of ethanol (100 ml) and acetic acid (50 ml) was dissolved the compound of Reference Example 41 (35.4 g). To the solution was added, under hydrogen atmosphere, 10% palladium-carbon (3.5 g), and the mixture was subjected to catalytic reduction at room temperature for 4 hours.

The catalyst was filtered off and washed sufficiently with tetrahydrofuran. The filtrate and the washing were combined and concentrated to dryness to obtain the above-titled compound (23.3 g).

NMR (90MHz, CDCl$_3$): δ 0.87(3H), 1.10–1.83(34H), 3.28–3.60(4H), 3.76–4.13(3H).

REFERENCE EXAMPLE 43

Production of 3-hydroxy-4-octadecyloxybutyl p-toluenesulfonate

In a mixture of dichloromethane (500 ml) and tetrahydrofuran (15 ml) was dissolved the compound of Reference Example 42 (18.3 g). To the solution was added dropwise, under ice-cooling, a solution of triethylamine (17.9 ml) and p-toluenesulfonyl chloride (11.6 g) in dichloromethane (100 ml). The reaction mixture was stirred at the same temperature for one hour, and then allowed to stand at room temperature for 57 hours. The reaction mixture was washed with water, 0.5N hydrochloric acid and water, dried and concentrated to dryness. The residue was purified by means of a silica gel column chromatography [carrier ; 650 g, developing solvent; hexane: ethyl acetate:acetone=4:1:0→4:1:1] to obtain the above-titled compound (10.75 g).

IR (KBr): γ 2970, 2920, 2860, 1470, 1355, 1185, 1175, 1142, 1120, 1105, 965, 957, 842, 655 cm$^{-1}$.

NMR (90MHz, CDCl$_3$): δ 0.86(3H), 1.14–1.94(34H), 2.44(3H), 3.10–3.57(4H), 4.50(1H), 4.20(2H), 7.24–7.45(2H), 7.74–7.95(2H).

REFERENCE EXAMPLE 44

Production of 2-[2-[3-hydroxy-4-(octadecyloxy)-butylthio]ethoxy]ethyl tetrahydropyranyl ether In the same manner as that of Reference Example 1, the above-titled compound (9.88 g) was obtained from the compound of Reference 43 (10.72 g) and 2-(2-mercaptoethoxy)ethyl tetrahydropyranyl ether (6.73 g).

IR (KBr): γ 2960, 2930, 2860, 1465, 1200, 1122, 1078, 1035 cm$^{-1}$.

NMR (90MHz, CDCl$_3$): δ 0.87(3H), 1.11–1.92(42H), 2.61–2.83(4H),3.14–4.06(11H), 4.64(1H).

REFERENCE EXAMPLE 45

Production of 2-[2-[4-octadecyloxy-3-(pyrimidin-2-yloxy)butylthio]ethoxy]ethanol In the same manners as those of Reference Examples 2 and 3, the above-titled compound (6.73 g) was obtained from the compound of Reference Example 44 (9.84 g) and 2-chloropyrimidine (2.68 g).

IR (KBr): γ 2930, 2850, 1580, 1463, 1440, 1420, 1322, 1125, 1110, 950 cm$^{-1}$.

NMR (90MHz, CDCl$_3$): δ 0.86(3H), 0.99–1.71(32H), 1.92–2.22(2H), 2.61–2.82(4H), 2.29–3.84(10H), 5.42(1H), 6.91(1H), 8.51(2H).

REFERENCE EXAMPLE 46

Production of 2-[2-[4-octadecyloxy-3-(pyrimidin-2-yloxy)butylsulfinyl]ethoxy]ethanol In the same manner as that of Reference Example 4, the above-titled compound (3.23 g) was obtained from the compound of Reference Example 45 (3.50 g) and m-chloroperbenzoic acid (1.35 g).

IR (KBr): γ 2925, 2860, 1580, 1565, 1465, 1420, 1320, 1120, 1015 cm$^{-1}$.

NMR (90MHz, CDCl$_3$): δ 0.87(3H), 1.08–1.86(32H), 2.10–2.46(2H), 2.73–3.21(4H), 3.36–4.03(10H), 5.26–5.63(1H), 6.93(1H), 8.50(2H).

REFERENCE EXAMPLE 47

Production of 2-[2-[4-octadecyloxy-3-(pyrimidin-2-yloxy) butylsulfinyl]ethoxy]ethyl methanesulfonate In the same manner as that of Reference Example 5, the above-titled compound (3.65 g) was obtained from the compound of Reference Example 46 (3.20 g) and methanesulfonyl chloride (0.67 ml).

NMR (90MHz, CDCl$_3$): δ 0.87(3H), 1.16–1.72(32H), 2.09–2.45(2H), 2.72–3.31(4H), 3.05(3H), 3.36–4.05 (8H), 4.29–4.46(2H), 5.48(1H), 6.93(1H), 8.50(2H) /

REFERENCE EXAMPLE 48

Production of 1-benzyloxymethyl-2-octadecyloxyethoxyacetic acid

In the same manner as that of Reference Example 2, the above-titled compound (1.0 g) was obtained from 1-benzyl-3-octadecylglycerol (1.0 g) and iodoacetic acid (0.93 g).

IR (Neat): γ 3200, 2925, 2860, 1760, 1740, 1465, 1370, 1235, 1105, 735, 695 cm$^{-1}$.

NMR (90MHz, CDCl$_3$): δ 0.87(3H), 1.20–1.70(32H), 3.40–3.80(7H), 4.25 (2H), 4.57(2H), 7.33(5H).

REFERENCE EXAMPLE 49

Production of methyl 1-benzyloxymethyl-2-octadecyloxyethoxyacetate

The compound of Reference Example 48 (1.0 g) was dissolved in methanol (10 ml) containing 9% of hydrogen chloride, and the reaction mixture was stirred for 3 hours at room temperature. To the reaction mixture was added dichloromethane (150 ml). The mixture was washed with water and dried, and then the solvent was distilled off to obtain the above-titled compound (0.81 g).

IR (Neat): γ 2920, 2830, 1760, 1465, 1210, 1115, 730, 695 cm$^{-1}$.

NMR (90MHz, CDCl$_3$): δ 0.87(3H), 1.20–1.70(32H), 3.33–3.90(10H), 4.30(2H), 4.53(2H), 7.30(5H)

REFERENCE EXAMPLE 50

Production of methyl 1-methanesulfonyloxymethyl-2-octadecyloxyethoxyacetate

The compound of Reference Example 49 (3.13 g) was dissolved in a mixture of methanol (15 ml) and tetrahydrofuran (15 ml). To the solution was added, under hydrogen atmosphere, 10% palladium-carbon (500 mg), and the mixture was subjected to catalytic reduction at room temperature overnight. The catalyst was filtered off, and the filtrate was subjected to distillation under reduced pressure to give a crude product of methyl 1-hydroxymethyl-2-octadecyloxyethoxyacetate (2.57 g). This product was, in the same manner as that of Reference Example 5, treated with methanesulfonyl chloride (1.06 g) to obtain the above-titled compound (2.1 g).

IR (Neat): γ 2920, 2860, 1755, 1465, 1350, 1215, 1175, 1130, 965, 820 cm$^{-1}$.

NMR (90MHz, CDCl$_3$): δ 0.87(3H), 1.20–1.70(32H), 3.07 (3H), 3.37–3.97(8H), 4.20–4.60(4H)

REFERENCE EXAMPLE 51

Production of methyl 1-[2-(2-hydroxyethoxy)ethyl]-thiomethyl-2-octadecyloxyethoxyacetate In the same manners as those of Reference Examples 1 and 3, the above-titled compound (1.1 g) was obtained from the compound of Reference Example 50 (2.1 g)

and 2-(2-mercaptoethoxy)ethyl tetrahydropyranyl ether (1.1 g).

IR (Neat): γ 3430, 2920, 2850, 1750, 1460, 1205, 1115 cm$^{-1}$.

NMR (90MHz, CDCl$_3$): δ 0.87(3H), 1.20–1.70(32H), 2.37(1H), 2.73–2.87(4H), 3.33–3.87(14H}, 4.30(2H).

REFERENCE EXAMPLE 52

Production of methyl 1-[2-(2-methanesulfonyloxyethoxy)ethyl]thiomethyl-2-octadecyloxyethoxyacetate In the same manner as that of Reference Example 5, the above-titled compound (0.77 g) was obtained from the compound of Reference Example 51 (0.7 g) and methanesulfonyl chloride (0.23 g).

IR (Neat): γ 2925, 2860, 1755, 1465, 1345, 1210, 1170, 1120, 920, 805 cm$^{-1}$.

NMR (90MHz, CDCl$_3$): δ 0.87(3H), 1.22–1.72(32H), 2.73–2.87(4H), 3.06(3H), 3.33–3.83(12H), 4.27–4 45(4H).

REFERENCE EXAMPLE 53

Production of 2,3-epoxypropyl 3-(6-pentylnaphthalen-2-yl)propyl ether

In the same manner as that of Reference Example 12, the above-titled compound (1.55 g) was obtained from 3-(6-pentylnaphthalen-2-yl)propanol (1.5 g) and epichlorohydrin (1.63 g).

IR (Neat): γ 2930, 2870, 1605, 1505, 1465, 1110, 885, 815 cm$^{-1}$.

NMR (200MHz, CDCl$_3$): δ 0.90(3H), 1.30–1.38(4H), 1.62–1.76(2H), 1.93–2.07(2H), 2.60–2.89(6H), 3.14–3.19(1H), 3.35–3.60(3H), 3.68–3.76(1H), 7.31(2H), 7.57(2H), 7.70(2H).

REFERENCE EXAMPLE 54

Production of 2-[2-[2-hydroxy-3-[3-(6-pentylnaphthalen-2-yl)propyloxy]propylthio]ethoxy]ethyl tetrahydropyranyl ether In the same manner as that of Reference Example 1, the above-titled compound (2.10 g) was obtained from the compound of Reference Example 53 (1.55 g) and 2-(2-acetylthioethoxy)ethyl tetrahydropyranyl ether (1.48 g).

IR (Neat): γ 3460, 2930, 2870, 1605, 1505, 1465, 1450, 1350, 1200, 1120, 1075, 1035, 815 cm$^{-1}$.

NMR (200MHz, CDCl$_3$): δ 0.89(3H), 1.27–2.07(14H), 2.62–2.86(8H), 2.97(1H), 3.42–3.73(10H), 4.63(1H), 7.30(2H), 7.57(2H), 7.70(2H).

REFERENCE EXAMPLE 55

Production of 2-[2-[3-(6-pentylnaphthalen-2-yl)propyloxy-2-(pyrimidin-2-yloxy)propylthio]ethoxy]ethanol In the same manner as that of Reference Example 7, the above-titled compound (1.0 g) was obtained from the compound of Reference Example 54 (2.0 g) and 2-chloropyrimidine (0.66 g).

IR (Neat): γ 3400, 2930, 2870, 1605, 1575, 1560, 1420, 1315, 1120, 1045, 810 cm$^{-1}$.

NMR (200MHz, CDCl$_3$): δ 0.89(3H), 1.30–1.36(4H), 1.62–1.75(2H), 1.87–2.00(2H), 2.53(1H), 2.70–3.00 (8H), 3.74–3.80(10H), 5.49(1H), 6.93(1H), 7.25–7.32(2H), 7.56(2H), 7.69(2H), 8.51(2H).

REFERENCE EXAMPLE 56

Production of 2-[2-[3-(6-pentylnaphthalen-2-yl)propyloxy-2-(pyrimidin-2-yloxy)propylsulfinyl]ethoxy]ethanol In the same manner as that of Reference Example 4, the above-titled compound (0.82 g) was obtained from the compound of Reference Example 55 (1.0 g) and m-chloroperbenzoic acid (0.41 g).

IR (Neat): γ 3370, 2930, 2870, 1575, 1565, 1420, 1315, 1120, 1040, 815 cm$^{-1}$.

NMR (200MHz, CDCl$_3$): δ 0.89(3H), 1.28–1.40(4H), 1.63–1.75(2H), 1.90–2.05(2H), 2.70–4.00(19H), 5.73–5.86(1H), 6.97(1H), 7.24–7.33(2H), 7.56(2H), 7.68(2H), 8.52(2H).

REFERENCE EXAMPLE 57

Production of 2-[2-[3-(6-pentylnaphthalen-2-yl)propyloxy-2-(pyrimidin-2-yloxy)propylsulfinyl]ethoxy]ethyl methanesulfonate In the same manner as that of Reference Example 5, the above-titled compound (0.90 g) was obtained from the compound of Reference Example 56 (0.81 g) and methanesulfonyl chloride (0.31 g).

IR (Neat): γ 2940, 2870, 1575, 1565, 1420, 1350, 1310, 1170, 1120, 1015, 920, 810 cm$^{-1}$.

NMR (200MHz, CDCl$_3$): δ 0.89(3H), 1.30–1.40(4H), 1.63–2.03(4H), 2.71–3.97(19H), 4.30–4.37(2H), 5.72–5.88(1H), 6.94–7.00(1H), 7.25–7.33(2H), 7.56(2H), 7.69(2H), 8.52(2H).

REFERENCE EXAMPLE 58

Production of 2-(2-hydroxy-3-octadecyloxypropylthio)ethyl triphenylmethyl ether

In toluene (5 ml) were dissolved 1,2-epoxy-3-octadecyloxypropane (9.85 g), 2-mercaptoethanol (2.4 g) and triethylamine (1.5 ml), and the solution was stirred for 2 hours at 55°–60° C. The reaction mixture was cooled, and then ethyl acetate (100 ml) and hexane (100 ml) were added. The mixture was washed with 0.001N sodium hydroxide (50 ml) and water (50 ml). The solvent was distilled off under reduced pressure to give a crude product of 2-(2-hydroxy-3-octadecyloxypropylthio)ethanol. The whole amount of this crude product was dissolved in pyridine (25 ml). To the solution was added triphenylmethyl chloride (12.5 g), and the mixture was stirred for 13 hours at 50° C. To the reaction mixture was added methanol (10 ml), and the resulting mixture was stirred at 60° C. for 0.5 hour, and then the mixture was concentrated to dryness. The residue was dissolved in a mixture of ethyl acetate (100 ml) and hexane (100 ml). The solution was washed with water, and concentrated to dryness under reduced pressure. The residue was purified by means of a silica gel column chromatography [carrier; 700 g, developing solvent ; hexane: ethyl acetate =9:1–4:1] to obtain the above-titled compound (13.4 g).

IR (Neat): γ 3460, 3060, 3025, 2925, 2860, 1490, 1465, 1445, 1115, 1090, 1060, 1030, 770, 755, 740, 700 cm$^{-1}$.

NMR (90 MHz, CDCl$_3$): δ 0.87(3H), 1.27(32H), 2.53–2.80 (5H), 3.20–3.53(6H), 3.63–3.93(1H), 7.20–7.57(15H).

REFERENCE EXAMPLE 59

Production of 2-[3-octadecyloxy-2-(pyrimidin-2-yloxy)propylthio]ethanol

In the same manner as that of Reference Example 2, 2-[3-octadecyloxy-2-(pyrimidin-2-yloxy)propylthio]ethyl triphenylmethyl ether was obtained from the compound of Reference Example 58 (9.17 g) and 2-chloropyrimidine (2.18 g). The product thus obtained was, in the same manner as that of Reference Example 3, subjected to a deprotection reaction to give the above-titled compound (4.85 g).

IR (Neat): γ 3350, 2925, 2855, 1575, 1560, 1465, 1420, 1310, 1120, 1070, 1040 cm$^{-1}$.

NMR ((90 MHz, CDCl$_3$): δ 0.87(3H), 1.23(32H), 2.00(1H), 2.80(2H), 2.90(2H), 3.47(2H), 3.77(4H), 5.40(1H), 6.93(1H), 8.53(2H).

REFERENCE EXAMPLE 60

Production of 2-[2-[2-[3-octadecyloxy-2-(pyrimidin-2-yloxy)propylthio]ethylthio]ethoxy]ethanol In the same manner as that of Reference Example 5, 2-[2-[2-[3-octadecyloxy-2-(pyrimidin-2-yloxy)propyl-thio]ethylthio]ethoxy]ethyl methanesulfonate was obtained from the compound of Reference Example 59 (4.8 g) and methanesulfonyl chloride (1.38 g). This product was, in the same manner as that of Reference Example 36, treated with 2-(2-acetylthioethoxy)ethyl tetrahydropyranyl ether (3.0 g) to give the above-titled compound (2.04 g).

IR (Neat): γ 3430, 2930, 2860, 1580, 1565, 1465, 1425, 1310, 1120, 1070, 1045 cm$^{-1}$.

NMR (90 MHz, CDCl$_3$-D$_2$O): δ 0.87(3H), 1.23(32H), 2.67-2.97(8H), 3.40-3.80(10H), 5.40(1H), 6.93(1H), 8.53(2H).

REFERENCE EXAMPLE 61

Production of 2-[2-[2-[3-octadecyloxy-2-(pyrimidin-2-yloxy) propylthio]ethylthio]ethoxy]ethyl methanesulfonate In the same manner as that of Reference Example 5, the above-titled compound (2.3 g) was obtained from the compound of Reference Example 60 (2.0 g).

IR (Neat): γ 2925, 2860, 1575, 1565, 1465, 1420, 1350, 1330, 1320, 1170, 1120, 1010, 970, 920, 805 cm$^{-1}$.

NMR (90 MHz, CDCl$_3$): δ 0.87(3H), 1.27(32H), 2.63-3.00 (8H), 3.07(3H), 3.47(2H), 3.67-3.80(6H), 4.30-4.40 (2H), 5.40(1H), 6.93(1H), 8.53(2H).

REFERENCE EXAMPLE 62

Production of 2-[2-[2-[3-octadecyloxy-2-(pyrimidin-2-yloxy)propylsulfinyl]ethylsulfinyl]ethoxy]ethyl methanesulfonate In the same manner as that of Reference Example 4, the above-titled compound (16.3 g) was obtained from the compound of Reference Example 61 (1.70 g) and m-chloroperbenzoic acid.

IR (Nujol): γ 1575, 1565, 1420, 1370, 1345, 1325, 1310, 1170, 1120, 1030, 1010 cm$^{-1}$.

NMR (90 MHz, CDCl$_3$): δ 0.87(3H), 1.27(32H), 2.90-3.53 (10H), 3.03(3H), 3.70-3.80(4H), 3.93(2H), 4.37(2H), 5.70(1H), 7.00(1H), 8.57(2H).

EXAMPLE 1

Production of 2-[2-[3-octadecyloxy-2-(pyrimidin-2-yloxy)propylsulfinyl]ethoxy]ethylthiazolium chloride The compound of Reference Example 5 (2.97 g) was dissolved in thiazole (5 ml). The solution was stirred at 80° C. overnight, then at 100° C. for 4.5 hours. Thiazole was distilled off under reduced pressure, and the residue was dissolved in dichloromethane. To the solution was added a small volume of ethanol, and the mixture was washed with a saturated aqueous saline solution. The washed layer was subjected to re-extraction with dichloromethane. The dichloromethane layers were combined, dried and concentrated to dryness. The residue was purified by means of a silica gel column chromatography [carrier; 90 g, developing solvent:chloroform:methanol:water=5:1:0–65:25:4] to give the above-titled compound [0.92 g].

IR (KBr): γ 3420, 2920, 2860, 1578, 1465, 1420, 1310, 1120, 1035 cm$^{-1}$.

NMR (90 MHz, CDCl$_3$-CD$_3$OD): δ 0.87(3H), 1.13-1.80(32H), 3.00-4.07(12H), 4.75-4.91(2H),5.-60-5.87(1H), 7.10 (1H), 8.21(1H), 8.43-8.67(3H).

EXAMPLE 2

Production of N-[2-[2-[3-octadecyloxy-2-(pyrimidin-2-yloxy) propylsulfinyl]ethoxy]ethyl]pyridinium chloride The compound of Reference Example 5 (1.30 g) was dissolved in pyridine (4 ml). The solution was stirred at 60° C. for one hour, at 0° C. overnight and then at 100° C. for 4.5 hours. Pyridine was distilled off under reduced pressure, and the residue was dissolved in dichloromethane (100 ml). To the solution was added a small volume of ethanol, and the mixture was washed with a saturated aqueous saline solution. To the washing was added a small volume of ethanol, and the mixture was subjected to re-extraction with dichloromethane. The dichloromethane layers were combined, dried and concentrated to dryness. The residue was purified by means of a silica gel column chromatography [carrier; 52 g, developing solvent; chloroform:methanol:water=6:1:0→65:25:2] to give the above-title compound (0.92 g).

IR (KBr): γ 3425, 2925, 2850, 1630, 1575, 1420, 1310, 1120, 1030 cm$^{-1}$.

NMR (200 MHz,CDCl$_3$): δ 0.88(3H), 1.26(30H), 1.53(2H), 2.80-4.30(12H), 5.29(2H), 5.71(1H), 7.07(1H), 8.01(2H), 8.34-8.62(3H), 9.62(2).

EXAMPLE 3

Production of 3-(3-hydroxypropyl)-1-[2-[2-[3-octadecyloxy-2-(pyrimidin-2-yloxy)propylsulfinyl]ethoxy]-ethyl]pyridinium chloride To the compound of Reference Example 5 (1.0 g) was added 3-(3-hydroxypropyl)pyridine (0.44 g), and the mixture was stirred at 70° C. overnight. The reaction mixture was dissolved in dichloromethane (100 ml), to which were added 2N hydrochloric acid (0.8 ml)) and a small volume of ethanol. The mixture was washed with a saturated aqueous saline solution. To the washing were added a small volume of ethanol and water, and the mixture was again subjected to extraction with dichloromethane (50 ml×2). The organic layers were combined, dried and concentrated to dryness, and the residue was purified by means of a silica gel column chromatography [carrier; 32 g, developing solvent; chloroform:methanol:water=5:1:0→65:25:3] to give the above-titled compound (0.30 g).

IR (KBr): γ 3375, 2940, 2875, 1585, 1575, 1475, 1430, 1320, 1125, 1045 cm$^{-1}$.

NMR (90 MHz, CDCl$_3$): δ 0.86(3H), 1.24(32H), 1.53(2H), 1.93(2H), 2.60-4.26(14H), 5.16(2H), 5.50-5.87(1H), 7.01(1H), 7.88(1H), 8.27(1H), 8.43-8.68(2H), 9.12 (1H), 9.45(1H).

EXAMPLE 4

Production of N-[2-[2-[3-octadecyloxy-2-(pyrimidin-2-yloxy) propylsulfinyl]ethoxy]ethyl]isoquinolinium chloride To the compound of Reference Example 5 (1.20 g) was added isoquinoline (0.40 g), and the mixture was stirred at 60° C. for one hour and at 80° C. for 3 hours. The reaction mixture was dissolved in dichloromethane (100 ml). To the solution were added 2N hydrochloric acid (0.58 ml) and a small volume of ethanol, and the mixture was washed with a saturated aqueous saline solution. To the washing was added a small volume of ethanol, and the mixture was again subjected to extraction with dichloromethane (100 ml×2). The organic layers were combined, dried and concentrated to dryness. The residue was purified by means of a silica gel column chromatography [carrier; 35 g, developing solvent; chloroform:methanol:water=10:1:0→65:25:2] to give the above-titled compound (0.48 g).

IR (KBr): γ 3450, 2940, 2875, 1650, 1585, 1570, 1475, 1430, 1320, 1120, 1045 cm$^{-1}$.

NMR (90 MHz, CDCl$_3$): δ 0.87(3H), 1.24(30H), 1.49(2H), 2.77–4.28(12H), 5.34(2H), 5.53–5.82(1H), 6.90–7.07(1H), 7.68–8.35(4H), 8.40–8.73(3H), 8.93–9.13(1H), 10.87–11.00(1H).

EXAMPLE 5

Production of N-[2-[2-[3-octadecyloxy-2-(pyrimidin-2-yloxy) propylsulfinyl]ethoxy]quinolinium chloride In the same manner as that of Example 4, the above-titled compound (0.20 g) was obtained from the compound of Reference Example 5 (0.65 g) and quinoline (1.32 g).

IR (KBr)P γ 3425, 2925, 1580, 1570, 1425, 1315, 1115, 1030, 1015 cm$^{-1}$.

NMR (90 MHz, CDCl$_3$): δ 0.86(3H), 1.23(30H), 1.56(2H), 2.82–4.35(12H), 5.52–5.88(3H), 7.00(1H), 7.72–7.98(1H), 7.98–8.33(3H), 8.33–8.76(3H), 8.80–9.05(1H), 10.03–10.25(1H).

EXAMPLE 6

Production of 5-(2-hydroxyethyl)-4-methyl-3-[2-[2-[3-octadecyloxy-2-(pyrimidin-2-yloxy)propylsulfinyl]ethoxy]-ethyl]thiazolium chloride.

In the same manner as that of Example 3, the above-titled compound (0.15 g) was obtained from the compound of Reference Example 5 (0.36 g) and 5-(2-hydroxyethyl)-4-methylthiazole (1.3 g).

IR (Nujol)P γ 3370, 1570, 1565, 1560, 1420, 1370, 1310, 1110, 1030 cm$^{-1}$.

NMR (90 MHz, CDCl$_3$-CD$_3$OD): δ 0.87(3H), 1.23(32H), 2.50(3H), 2.60–3.27(6H), 3.47(2H), 3.70–4.10(8H), 4.73(2H), 5.70(1H), 7.03(1H), 8.57(2H), 10.20–10.30(1H).

EXAMPLE 7

Production of 4-dimethylamino-1-[2-[2-[3-octadecyloxy-2-(pyrimidin-2-yloxy)propylsulfinyl]ethoxy]ethyl]pyridinium chloride In toluene were dissolved the compound of Reference Example 5 (0.67 g) and dimethylaminopyridine (0.53 g). The solution was stirred at 50° C. overnight, and then at 78° C. for 1.5 hour. toluene was distilled off under reduced pressure, and the residue was dissolved in dichloromethane (100 ml). To the solution were added 2N hydrochloric acid and a small volume of ethanol, and the mixture was washed with a saturated aqueous saline solution. The organic layer was dried and concentrated to dryness. The residue was purified by means of a silica gel column chromatography [carrier; 25 g, developing solvent; chloroform:methanol:water=10:1:0→65:25:1] to obtain the above-titled compound (0.39 g).

IR (KBr): γ 3460, 3440, 2940, 2875, 1660, 1585, 1475, 1430, 1320, 1185, 1120, 1040 cm$^{-1}$.

NMR (90 MHz, CDCl$_3$): δ 0.87(3H), 1.25(30H), 1.57(2H), 2.70–4.07(12H), 3.23(6H), 4.69(2H), 5.63–5.93(1H), 6.80–6.97(2H), 7.00(1H), 8.40–8.58(2H), 8.58–8.68(2H).

EXAMPLE 8

Production of N-[2-[2-[3-octadecyloxy-2-(pyrimidin-2-yloxy)propylthio]ethoxy]ethyl]imidazole.

In the same manner as that of Reference Example 5, 2-[2-[3-octadecyloxy-2-(pyrimidin-2-yloxy)propylthio]-ethoxy]ethyl methanesulfonate (1.87 g) was obtained from the compound of Reference Example 3 (1.65 g) and methane-sulfonyl chloride (0.54 g). The whole amount of this product and imidazole (0.62 g) were stirred for 2 hours at room temperature in dimethylsulf-oxide (10 ml) in the presence of sodium hydride (0.37 g). To the reaction mixture was added water, and the mixture was subjected to extraction with a mixture of hexane-ethyl acetate. The extract was washed with water, dried and concentrated to dryness to obtain the above-titled compound (1.78 g).

IR (Film): γ 2925, 2850, 1680, 1660, 1605, 1465, 1420, 1310, 1280, 1230, 1120 cm$^{-1}$.

NMR (90 MHz, CDCl$_3$): δ 0.87(3H), 1.25(32H), 2.78(2H), 2.91(2H), 3.37–3.80(8H), 4.07(2H), 5.40(1H), 6.92(1H), 6.99(1H), 7.03(1H), 7.52(1H), 8.48(2H).

EXAMPLE 9

Production of 6-[3-[2-[2-[3-octadecyloxy-2-(pyrimidin-2-yloxy)propylthio]ethoxy]ethyl]imidazolio-1-yl]hexanoate To the compound of Example 8 (1.0 g) was added methyl 6-bromohexanoate (0.87 g), and the mixture was heated at 80° C. for 4 hours. The reaction mixture was cooled, and ether was added, and then the supernatant was removed. The residue was dissolved in methanol (12 ml), and a 2N sodium hydroxide solution (3.0 ml) was added to the solution, and then the mixture was stirred at room temperature for 2 hours. To the resulting mixture was then added 1N hydrochloric acid (6.0 ml), and the mixture was subjected to extraction with dichloromethane. The extract was washed with an aqueous solution of sodium bicarbonate and an aqueous saline solution, dried and concentrated to dryness. The residue was purified by means of a silica gel column chromatography [carrier; 50 g, developing solvent; chloroform:methanol:water=65:25:4] to obtain the above-titled compound (0.70 g).

IR (KBr): γ 3420, 2925, 2850, 1575, 1560, 1462, 1420, 1310, 1115 cm$^{-1}$.

NMR(200 MHz, CDCl$_3$): δ 0.88(3H), 1.25(36H), 1.80–2.00(2H), 2.10–2.30(2H), 2.70–2.90(4H)), 3.46(2H), 3.65(2H), 3.74(2H), 3.83(2H), 4.31(2H), 4.60(2H), 5.39(1H), 6.99(1H), 7.54(1H), 7.58(1H), 8.53(2H), 10.01(1H).

EXAMPLE 10

Production of 6-[3-[2-[2-[3-octadecyloxy-2-(pyrimidin-2-yloxy)propylsulfinyl]ethoxy]ethyl]imidazolio-1-yl]hexanoate The compound of Example 9 (0.59 g) was dissolved in dichloromethane (15 ml), to which was portionwise added, while stirring under ice-cooling, meta-chloroperbenzoic acid (162 mg). The reaction mixture was washed with an aqueous solution of sodium bicarbonate, dried and concentrated to dryness. The residue was purified by means of silica gel column chromatography [carrier; 35 g, developing solvent; chloroform- :methanol:water=65:25:4] to obtain the above-titled compound (0.38 g).

IR (KBr): γ 2925, 2850, 1575, 1565, 1465, 1420, 1310, 1160, 1120, 1030 cm$^{-1}$.

NMR (200 MHz, CDCl$_3$): δ 0.88(3H), 1.25(32H), 1.45–2.0(6H), 2.15–2.3(2H), 2.85–3.55(6H), 3.70–4.05(2H), 4.31(2H), 4.60(2H), 5.76(1H), 7.01(1H), 7.45(1H), 8.54(2H), 10.59(1H).

EXAMPLE 11

Production of 4-[3-[2-[2-[3-octadecyloxy-2-(pyrimidin-2-yloxy)propylthio]ethoxy]ethyl]imidazolio-1-yl]butyrate In the same manner as that of Example 9, the above-titled compound (0.39 g) was obtained from the compound of Example 8 (0.72 g) and ethyl 4-bromobutyrate (0.60 g).

IR (KBr): γ 3440, 2930, 2860, 1578, 1565, 1470, 1420, 1310, 1120 cm$^{-1}$.

NMR (200 MHz, CDCl$_3$): δ 0.88(3H), 1.25(32H), 2.00–2.25(4H), 2.75–3.00(4H), 3.47(2H), 3.65(2H), 3.73(2H), 3.83(2H), 4.37(2H), 4.57(2H), 5.39(1H), 6.99(1H), 7.54(2H), 8.52(2H), 10.04(1H).

EXAMPLE 12

Production of N-[3-[3-[3-octadecyloxy-2-(pyrimidin-2-yloxy) propylthio]propoxy]propyl]imidazole In the same manner as that of Example 8, the above-titled compound (1.38 g) was obtained by converting the compound of Reference Example 7 (1.24 g) into the methanesulfonyl compound, and then by allowing the compound to react with imidazole.

IR (Film): γ 2925, 2855, 1578, 1560, 1462, 1420, 1312, 1110 cm$^{-1}$.

NMR (90 MHz, CDCl$_3$): δ 0.87(3H), 1.25(32H), 1.70–2.10(4H), 2.70(2H), 2.88(2H), 3.23–3.56(6H), 3.79(2H), 4.02(2H), 5.40(1H, 6.89(2H), 7.03(1H), 7.45(1H), 8.47(2H).

EXAMPLE 13

Production of 6-[3-[3-[3-octadecyloxy-2-(pyrimidin-2-yloxy)propylthio]propoxy]propyl]imidazolio-1-yl]hexanoate In the same manner as that of Example 9, the above-titled compound (0.78 g) was obtained from the compound of Example 12 (1.38 g) and methyl 6-bromohexanoate.

IR (Film): γ 2925, 2850, 1720, 1572, 1560, 1460, 1418, 1158, 1010 cm$^{-1}$.

NMR (90 MHz, CDCl$_3$): δ 0.88(3H), 1.25(32H), 1.45–2.05(8H), 2.18(2H), 2.35(2H), 2.67(2H), 2.89(2H), 3.35–3.80(8H), 4.30–4.50(4H), 5.41(1H), 6.99(1H), 7.40(1H), 7.54(1H, 8.52(2H), 10.02(1H).

EXAMPLE 14

Production of 6-[3-[3-[3-octadecyloxy-2-(pyrimidin-2yloxy)propylsulfinyl]propoxy]propyl]imidazolio-1-yl]-hexanoate In the same manner as that of Example 10, the above-titled compound (0.38 g) was obtained from the compound of Example 13 (0.59 g).

IR (Film): γ 2925, 2850, 1578, 1560, 1465, 1420, 1312, 1160, 1115, 1010 cm$^{-1}$.

NMR (200 MHz, CDCl$_3$): δ 0.88(3H), 1.25(32H), 1.50–2.10(8H), 2.10–2.30(4H), 2.85(2H), 3.04–3.60(8H), 4.32(2H), 4.44(2H), 5.74(1H), 6.99(1H), 7.19(1H), 7.30(1H), 8.53(2H), 10.68(1H).

EXAMPLE 15

Production of 3-[3-[3-octadecyloxy-2-(pyrimidin-2-yloxy) propylsulfonyl]propoxy]propylthiazolium chloride In the same manner as that of Example 1, the above-titled compound (0.62 g) was obtained from the compound of Reference Example 9 (2.10 g) and thiazole (4.0 ml).

IR (KBr): γ 3420, 2925, 2855, 1630, 1578, 1462, 1420, 1310, 1120 cm$^{-1}$.

NMR (90 MHz, CDCl$_3$): δ 0.87(3H), 1.05–2.20(44H), 2.98–3.80(12H), 4.86(2H), 5.76(1H), 7.02(1H), 8.26(1H), 8.50(1H), 8.55(2H), 11.63(1H).

EXAMPLE 16

Production of N-[3-[3-[3-octadecyloxy-2-(pyrimidin-2-yloxy) propylsulfonyl]propoxy]propyl]pyridinium chloride In the same manner as that of Example 2, the above-titled compound (0.77 g) was obtained from the compound of Reference Example 9 (1.0 g) and pyridine (4.0 ml).

IR (KBr): γ 3430, 2925, 2850, 1630, 1580, 1420, 1310, 1120 cm$^{-1}$.

NMR (90 MHz, CDCl$_3$): δ 0.87(3H), 1.13–2.26(44H), 3.00–3.83(12H), 5.01(2H), 5.76(1H), 7.01(1H), 8.09(2H), 8.45(1H), 8.52(2H), 9.56(2H).

EXAMPLE 17

Production of N-[3-[3-[3-octadecyloxy-2-(pyrimidin-2-yloxy) propylsulfonyl]propoxy]propyl]-N,N,N-trimethylammonium chloride The compound of Reference Example 9 (1.0 g) was dissolved in a toluene (5.0 ml) solution of trimethylamine (1.0 g), and the mixture was stirred at room temperature for 5 days. The reaction mixture was concentrated to dryness, and the residue was dissolved in dichloromethane (100 ml). The solution was washed with a saturated aqueous saline solution, dried and concentrated. The concentrate was subjected to re-precipitation from a mixture of chloroform and acetone to give the above-titled compound (0.65 g).

IR (KBr): γ 34.50, 2925, 2855, 1638, 1580, 1468, 1422, 1310, 1220 cm$^{-1}$.

NMR (90 MHz, CDCl$_3$): δ 0.87(3H), 1.13–1.83(32H), 1.83–2.30(4H), 3.10–3.90(14H), 3.43(9H), 5.78(1H), 7.03(1H), 8.54(2H).

EXAMPLE 18

Production of 3-[3-[3-octadecyloxy-2-(pyrimidin-2-yloxy) propylsulfinyl]propoxy]propylthiazolium chloride In the same manner as that of Example 1, the above-titled compound (1.26 g) was obtained from the compound of Reference Example 11 (2.10 g) and thiazole (4.0 ml).

IR (KBr): γ 3420, 2920, 2850, 1630, 1575, 1560, 1460, 1420, 1310, 1110, 1015 cm$^{-1}$.

NMR (90 MHz, CDCl$_3$): δ 0.87(3H), 1.10–2.30(44H), 2.77(2H), 3.0–3.60(8H), 3.77(2H), 4.87(2H), 5.75(1H), 6.98(1H), 8.21(1), 8.50(1H), 8.51(2H), 11.70(1H).

EXAMPLE 19

Production of 2-[2-[3-octadecyloxy-2-(pyrimidin-2-yl-oxy) propylsulfonyl]ethoxy]ethylthiazolium chloride In the same manner as that of Example 1, the above-titled compound (2.30 g) was obtained from the compound of Reference Example 15 (4.3 g) and thiazole (15 ml).

IR (KBr): γ 3420, 2920, 2850, 1632, 1575, 1465, 1420, 1310, 1290, 1120 cm$^{-1}$.

NMR (90 MHz, CDCl$_3$): δ 0.87(3H), 1.25(32H), 3.10–4.15(12H), 5.07–5.23(1H), 5.78(1H), 7.04(1H), 8.26(1H), 8.56(2H), 8.93(1H), 11.14(1).

EXAMPLE 20

Production of N-[2-[2-[3-octadecyloxy-2-(pyrimidin-2-yloxy) propylsulfonyl]ethoxy]ethyl]pyridinium chloride In the same manner as that of Example 2, the above-titled compound (0.48 g) was obtained from the compound of Reference Example 15 (1.0 g) and pyridine (5 ml).

IR (KBr): γ 3420, 2920, 2850, 1632, 1575, 1490, 1464, 1422, 1310, 1120 cm$^{-1}$.

NMR (90 MHz, CDCl$_3$): δ 0.87(3H), 1.25(32H), 3.10–4.23(12H), 4.93(2H), 5.80(1H), 7.11(1H), 8.06(2H), 8.53(1H), 8.57(2H), 9.12(2H). cl EXAMPLE 21

Production of N-[2-[2-[3-octadecyloxy-2-(pyrimidin-2-yloxy) propylsulfonyl]ethoxy]ethyl]-N,N,N-trimethylammonium chloride In the same manner as that of Example 17, the above-titled compound (0.58 g) was obtained from the compound of Reference Example 15 (1.0 g) and toluene (15 ml) containing trimethylamine (3.0 ).

IR (KBr): γ 3430, 2920, 2850, 1625, 1565, 1462, 1415, 1285, 1120 cm$^{-1}$.

NMR (90MHz, CDCl$_3$): δ 0.87(3H), 1.25(32H), 3.23(9H), 3.30–4.10(14H), 5.77(1H), 7.06(1H), 8.56(2H).

EXAMPLE 22

Production of N-methyl-N-[2-[2-[3-octadecyloxy-2-(pyrimidin-2-yloxy) propylthio]ethoxy]ethyl]pyrrolidinium chloride In the same manner as that of Example 1, the above-titled compound (0.63 g) was obtained from the compound of Reference Example 16 (1.0 g) and N-methylpyrrolidine (1.0 g).

IR (KBr): γ 3440, 2925, 2850, 1575, 1560, 1465, 1420, 1315, 1120 cm$^{-1}$.

NMR (90 MHz, CDCl$_3$): δ 0.87(3H), 1.04–1.69(32H), 2.34(4H), 2.69–3.00(4H), 3.23–4.14(14H), 3.32(3H), 5.39(1H), 6.96(1H), 8.51(2H).

EXAMPLE 23

Production of N-[2-[2-[3-octadecyloxy-2-(pyrimidin-2-yloxy) propylthio]ethoxy]ethyl]-N,N,N-trimethylammonium chloride In the same manner as that of Example 17, the above-titled compound (0.58 g) was obtained from the compound of Reference Example 16 (1.22 g) and a 30% aqueous trimethylamine solution (2.0 ml).

IR (KBr): γ 3460, 2920, 2850, 1580, 1565, 1482, 1465, 1420, 1336, 1315, 1135, 1120 cm$^{-1}$.

NMR (90 MHz, CDCl$_3$): δ 0.86(3H), 1.28(30H), 1.51(2H), 2.70–2.99(4H), 3.29–4.11(10H), 3.50(9H), 5.23–5.49(1H), 6.97(1H), 8.53(2H).

EXAMPLE 24

Production of N-[2-[2-[3-octadecyloxy-2-(pyrimidin-2-yloxy) propylsulfinyl]ethoxy]ethyl]-N,N,N-trimethylammonium chloride In the same manner as that of Example 17, the above-titled compound (0.34 g) was obtained from the compound of Reference Example 5 (1.0 g) and a 30% aqueous trimethylamine solution (1.6 ml).

IR (KBr): γ 3420, 2925, 2850, 1578, 1565, 1465, 1420, 1315, 1115, 1035, 1015 cm$^{-1}$.

NMR (200 MHz, CDCl$_3$): δ 0.87(3H), 1.26(30H), 1.51(2H), 2.83–3.25(4H), 3.25–3.58(4H), 3.40(9H), 3.70–3.82(2H), 3.87–4.23(4H), 5.63–5.86(1H), 6.98–7.10(1H), 8.56(2H).

EXAMPLE 25

Production of 1-[(5-ethoxycarbonyl)pentyl]-3-[2-[2-[3-octadecyloxy-2-(pyrimidin-2-yloxy)propylthio]ethoxy]ethyl]imidazolium chloride In the same manner as that of Example 1, the above-titled compound (992 mg) was obtained from the compound of Reference Example 16 (1.0 g) and ethyl 6-(imidazol-1-yl)hexanoate (0.76 g).

IR (KBr): γ 3475, 2930, 2870, 1740, 1580, 1565, 1465, 1425, 1315, 1162, 1118 cm$^{-1}$.

NMR (90 MHz, CDCl$_3$-CD$_3$OD): δ 0.88(3H), 1.03–2.43(43H), 2.66–3.03(4H), 3.31–4.43(12H), 4.65(2H), 5.39(1H), 6.95(1H), 7.24(1H), 7.64(1H), 8.50(2H), 10.72(1H).

EXAMPLE 26

Production of 1-[(3-ethoxycarbonyl-3-methyl)butyl]-3-[2-[2-[3-octadecyloxy-2-(pyrimidin-2-yloxy)propylthio]-ethoxy]ethyl]imidazolium choride In the same manner as that of Example 1, the above-titled compound (303 mg) was obtained from the compound of Reference Example 16 (0.64 g) and ethyl 2,2-dimethyl-4-(imidazol-1-yl)butyrate (0.42 g).

IR (Neat): γ 3400, 2930, 2860, 1725, 1575, 1562, 1420, 1310, 1162, 1135, 1110 cm$^{-1}$.

NMR (90 MHz, CDCl$_{32}$): δ 0.87(3H), 1.05–1.57(41H), 2.03–2.27(2H), 2.73–3.00(4H), 3.34–3.92(8H), 4.02–4.75(4H), 4.66(2H), 5.39(1H), 6.98(1H), 7.13–7.28(1H), 7.58(1H), 8.50(2H), 10.87(1H).

EXAMPLE 27

Production of 4-[3-[2-[2-[3-octadecyloxy-2-(pyrimidin-2-yloxy)propylthio]ethoxy]ethyl]imidazolio-1-yl]-2,2-dimethylbutyrate In the same manner as the hydrolysis reaction of ester in Example 9, the compound of Example 26 (0.28 g) was subjected to hydrolysis to obtain the above-titled compound (172 mg).

IR (KBr): γ 3420, 2925, 2860, 1575, 1560, 1420 cm$^{-1}$.

NMR (90 MHz, CDCl$_3$): δ 0.86(3H), 1.13(6H), 1.24(30H), 1.56(2H), 2.04(2H), 2.69–3.10(4H), 3.36–3.94(8H), 4.22–4.80(4H), 5.38(1), 6.94(1H), 7.41(1H), 7.53(1H), 8.48(2H), 10.13(1H).

EXAMPLE 28

Production of 4-[3-[2-[2-[3-(12-cyclohexyldodecyloxy)-2-(pyrimidin-2-yloxy)propylthio]ethoxy]ethyl]imidazolio-2-yl]butyrate In the same manner as that of Example 1, ethyl 4-[3-[2-[2-[3-(12-cyclohexyldodecyloxy)-2-(pyrimidin-2-yloxy)-propylthio]ethoxy]ethyl]imidazolio-1-yl]butyrate was obtained from the compound of Reference Example 19 (0.78 g) and ethyl 4-(imidazol-1-yl)butyrate (0.50 g). the whole amount of this product was subjected, in the same manner as that of Example 9, to hydrolysis of ester to give the above-titled compound (0.59 g).

IR (Neat): γ 3400, 3150, 2920, 2850, 1590, 1465, 1320, 1160, 1120, 1040, 805 cm$^{-1}$.

NMR (90 MHz, CDCl$_3$): δ 1.00–1.80(33H), 2.20(4H), 3.73–3.93(4H), 3.40–3.87(8H), 4.37(2H), 4.60(2H), 5.40(1H), 6.93(1H), 7.34(1H), 7.51(1H), 8.48(2H), 10.53(1H).

EXAMPLE 29

Production of 1-[2-[2-[3-(12-cyclohexyldodecyloxy)-2-(pyrimidin-2yloxy)propylsulfinyl]ethoxy]ethyl]-pyridinium chloride In the same manner as that of Example 2, the above-titled compound (0.53 g) was obtained from the compound of Reference Example 20 (0.95 g) and pyridine (2.0 ml).

IR (Neat): γ 3400, 2925, 2860, 1630, 1575, 1560, 1420, 1315, 1115, 1030, 770 cm$^{-1}$.

NMR (90 MHz, CDCl$_3$): δ 1.20–1.80(33H), 2.87–3.57(6H), 3.75–4.23(6H), 5.70(1H), 7.00(1H), 8.04(1H), 8.40(1H), 8.55(2H), 9.62(2H).

EXAMPLE 30

Production of N-methyl-N-[2-[2-[3-octadecyloxy-2-(pyrimidin-2-yloxy)propylsulfinyl]ethoxy]ethyl]pyrrolidinium chloride In the same manner as that of Example 1, the above-titled compound (0.1 g) was obtained from the compound of Reference Example 5 (0.8 g) and N-methylpyrrolidine (1.0 g).

IR (KBr): γ 3450, 2925, 2860, 1580, 1570, 1422, 1315, 1030 cm$^{-1}$.

NMR (90 MHz, CDCl$_3$-CD$_3$OD): δ 0.87(3H), 1.11–1.72(32H), 2.09–2.39(4H), 2.82–4.25(18H), 3.14(3H), 5.62–5.92(1H), 7.05(1H), 8.55(2).

EXAMPLE 31

Production of 4-[3-[2-[2-[3-octadecyloxy-2-(pyrimidin-4-yloxy)propylthio]ethoxy]ethyl]imidazolio-1-yl]butyrate In the same manner as that of Example 9, the above-titled compound (244 mg) was obtained from the compound of Reference Example 23 (730 mg) and ethyl 4-(imidazol-1-yl)-butyrate (660 mg).

IR (KBr): γ 3420, 2925, 2860, 2580, 2555, 1465, 1390, 1300, 1115, 985 cm$^{-1}$.

NMR (90 MHz, CDCl$_3$): δ 0.87(3H), 1.13–1.53(34H), 2.21(2H), 2.67–2.97(4H), 3.32–3.97(8H), 4.06–4.80(4H), 5.49(1H), 6.74(1H), 7.56(1H), 7.75(1H), 8.43(1H), 8.71(1H), 9.98(1H).

EXAMPLE 32

Production of N-[2-[2-[3-octadecyloxy-2-(pyrimidin-4-yloxy) propylthio]ethoxy]ethyl]pyridinium chloride In the same manner as that of Example 2, the above-titled compound (626 mg) was obtained from the compound of Reference Example 23 (900 mg) and pyridine (3.0 ml).

IR (KBr): γ 3440, 3410, 2920, 2850, 1580, 1463, 1390, 1300, 1120, 985 cm$^{-1}$.

NMR (90 MHz, CDCl$_3$): δ 0.87(3H), 1.08–1.78(32H)), 2.50–2.97(4H), 3.32–3.81(6H), 4.03(2H), 5.33(2H), 5.45(1H), 6.73(1H), 7.90–8.17(2H), 8.30–8.60(2H), 8.72(1H), 9.61(2H).

EXAMPLE 33

Production of 6-[3-[2-[2-[3-octadecyloxy-2-(pyrimidin-4-yloxy) propylthio]ethoxy]ethyl]imidazolio-1-yl]hexanoate In the same manner as that of Example 9, the above-titled compound (1.10 g) was obtained from the compound of Reference Example 23 (1.50 g) and ethyl 6-(imidazol-1-yl)-hexanoate (1.04 g).

IR (KBr): γ 3400, 2925, 2860, 1580, 1710, 1582, 1560, 1470, 1395, 1300, 1120 cm$^{-1}$.

NMR (90 MHz, CDCl$_3$-CD$_3$OD): δ 0.84(3H), 1.04–2.12(38H), 2.29(2H), 2.65–2.95(4H), 3.22–3.94(8H), 4.22(2H), 4.46(2H), 5.49(1H), 6.79(1H), 7.55(2H), 8.42(1H), 8.70(1H), 9.30–9.60(1H).

EXAMPLE 34

Production of N-[2-[2-[3-octadecyloxy-2-(pyrimidin-4-yloxy) propylsulfinyl]ethoxy]ethyl]pyridinium chloride In the same manner as that of Example 2, the above-titled compound (559 mg) was obtained from the compound of Reference Example 25 (1.00 g) and pyridine (3.0 ml).

IR (KBr): γ3410, 2920, 2850, 1578, 1462, 1198, 1110 cm$^{-1}$.

NMR (90 MHz, CDCl$_3$-CD$_3$OD): δ 0.87(3H), 1.07–1.67(32H), 2.74–4.17(12H), 4.80–5.03(2H), 6.73–6.99(1H), 7.90–8.18(2H), 8.28–8.87(3H), 9.08(2H).

EXAMPLE 35

Production of N-[2-[2-[3-octadecyloxy-2-(pyrimidin-4-yloxy) propylsulfinyl]ethoxy]ethyl]-N,N,N-trimethylammonium chloride In the same manner as that of Example 17, the above-titled compound (626 mg) was obtained from the compound of Reference Example 25 (1.00 g) and a 30% aqueous trimethylamine solution (1.6 ml).

IR (KBr): γ3425, 2920, 2850, 1580, 1463, 1390, 1300, 1110, 1030, 985 cm$^{-1}$.

NMR (90 MHz, CDCl$_3$): δ 0.87(3H), 1.00–1.77(32H), 2.87–4.30(14H), 3.47(9H), 585(1H), 6.81(1H), 8.50(1H), 8.80(1H).

EXAMPLE 36

Production of 6-[3-[2-[2-[3-octadecyloxy-2-(pyrimidin-4-yloxy)propylsulfinyl]ethoxy]ethyl]imidazolio-1-yl]hexanoate.

In the same manner as that of Example 9, the above-titled compound (114 mg) was obtained from the compound of Example 25 (900 mg).

IR (KBr): γ 3390, 2920, 2850, 1580, 1558, 1465, 1372, 1300, 1117, 1035, 984 cm$^{-1}$.

NMR (200 MHz, CDCl$_3$): δ 0.88(3H), 1.00–1.97(38H), 2.20(2H), 2.87–4.11(12H), 4.26(2H), 4.60(2H), 5.88(1H), 6.83(1H), 7.57(2H), 8.52(1H), 8.79(1H), 9.98(1H).

EXAMPLE 37

Production of 5-[1-[2-[2-[3-octadecyloxy-2-(pyrimidin-2-yloxy)propylthio]ethoxy]ethyl]pyridinio-3-yl]pentanoate In the same manner as that of Example 9, the above-titled compound (350 mg) was obtained from the compound of Reference Example 16 (606 mg) and ethyl 5-(pyridin-3-yl)-valerate (414 mg).

IR (Nujol): γ 3360, 1575, 1560, 1420, 1310, 1110 cm$^{-1}$.

NMR (90 MHz, CDCl$_3$-CD$_3$OD): δ 0.87(3H), 1.27–2.10(36H), 2.20(2H), 2.67–2.97(6H), 3.37–3.73(6H), 3.97(2H), 5.17(2H), 5.43(1H), 6.93(1H), 7.77(1H), 8.17(1H), 8.47(2H), 8.90(1H), 9.77(1H).

EXAMPLE 38

Production of 6-[3-[2-[2-[2-(pyrimidin-2-yloxy)-3-(3,7, 11,15-tetramethylhexadecyloxy)propylthio]ethoxy]ethyl]-imidazolio-1-yl)hexanoate In the same manner as that of Example 9, the above-titled compound (530 mg) was obtained from the compound of Reference Example 28 (633 mg) and ethyl 6-(imidazol-1-yl)-hexanoate (252 mg).

IT (Nujol): $\gamma$ 3400, 1580, 1565, 1425, 1380, 1370, 1120 cm$^{-1}$.

NMR (90 MHz, CDCl$_3$): $\delta$ 0.73–2.00(45H), 2.13–2.33(2H), 2.80(2H), 2.87(2H), 3.33–3.87(8H), 2.23(2H), 4.47(2H), 5.40(1H), 7.00(1H), 7.27(1H), 7.50(1H), 8.53(2H), 9.50(1H).

EXAMPLE 39

Production of N-[2-[2-[2-(pyrimidin-2-yloxy)-3-(3,7,11, 15-tetramethylhexadecyloxy)propylsulfinyl]ethoxy]ethyl]-pyridinium chloride In the same manner as that of Example 2, the above-titled compound (1.58 g) was obtained from the compound of Reference Example 30 (2.80 g) and pyridine (2 ml).

IR (Nujol): $\gamma$ 3400, 1580, 1565, 1490, 1425, 1380, 1310, 1120, 1040, 1020 cm$^{-1}$.

NMR (90 MHz, CDCl$_3$-CD$_3$OD): $\delta$ 0.77–1.70(39H), 3.00(2H), 3.13–4.10(10H), 5.00(2H), 5.53–5.87(1H), 7.03(1H), 8.03(2H), 8.30–8.50(1H), 8.57(2H), 9.20(2H).

EXAMPLE 40

Production of N-[5-[5-[3-octadecyloxy-2-(pyrimidin-2-yloxy) propylsulfinyl]pentyloxy]pentyl]thiazolium chloride In the same manner as that of Example 1, the above-titled compound (0.80 g) was obtained from the compound of Reference Example 33 (1.5 g) and thiazole (4.0 ml).

IR (KBr): $\gamma$ 3420, 2920, 2850, 1630, 1575, 1560, 1460, 1420, 1310, 1110, 1015 cm$^{-1}$.

NMR (90 MHz, CDCl$_3$): $\delta$ 0.87(3H), 1.10–2.30(44H), 2.77(2H), 3.00–3.60(8H), 3.77(2H), 4.87(2H), 5.75(1H), 6.98(1H), 8.21(1H), 8.50(1H), 8.51(2H), 11.70(1H).

EXAMPLE 41

Production of N-[5-[5-[3-octadecyloxy-2-(yrimidin-2-yloxy) propylsulfonyl]pentyloxy]pentyl]thiazolium chloride In the same manner as that of Example 1, the above-titled compound (1.53 g) was obtained from the compound of Reference Example 35 (2.1 g) and thiazole (5.0 ml).

IR (KBr): $\gamma$ 3420, 2925, 2855, 1630, 1578, 1462, 1420, 1310, 1120 cm$^{-1}$.

NMR (90 MHz, CDCl$_3$): $\delta$ 0.87(3H), 1.05–2.20(44H), 2.98–3.80(12H), 4.86(2H), 5.76(1H), 7.02(1H), 8.26(1H), 8.50(1), 8.55(2H), 11.63(1H).

EXAMPLE 42

Production of N-[5-[5-[3-octadecyloxy-2-(pyrimidin-2-yloxy) propylsulfonyl]pentyloxy]pentyl]pyridinium chloride In the same manner as that of Example 2, the above-titled compound (0.42 g) was obtained from the compound of Reference Example 35 (0.6 g) and pyridine (5 ml).

IR (KBr): $\gamma$ 3430, 2925, 2850, 1630, 1580, 1420, 1310, 1120 cm$^{-1}$.

NMR (90 MHz, CDCl$_3$): $\delta$ 0.87(3H), 1.13–2.26(44H), 3.00–3.83(12H), 5.01(2H), 5.76(1H), 7.01(1H), 8.09(2H), 8.45(1H), 8.52(2H),, 9.56(2H).

EXAMPLE 43

Production of N-[2-(2-methoxy-3-oxtadecyloxypropylthio)ethoxy]ethyl-N,N,N-trimethylammonium chloride In the same manner as that of Reference Example 5, 2-[2-(2-methoxy-3-octadecyloxypropylthio)ethoxy]ethyl methanesulfonate (2.25 g) was obtained from the compound of Reference Example 36 (2.0 g) and methanesulfonyl chloride (0.74 g). the whole amount of this product (0.82 g) was subjected to the same reaction as that of Example 17 to obtain the above-titled compound (0.50 g).

IR (KBr): $\gamma$ 3430, 2930, 2855, 1465, 1360, 1110, 955 cm$^{-1}$.

NMR (200 MHz, CDCl$_3$): $\delta$ 0.88(3H), 1.25(32H), 2.15(2H), 2.80(2H), 3.44(3H), 3.50(9H), 3.35–3.55(5H), 3.70(2H), 3.90–4.10(4H).

EXAMPLE 44

Production of N-[2-[2-(2-methoxy-3-octadecyloxypropylsulfinyl)ethoxy]ethyl]-N,N,N-trimethylammonium chloride In the same manner as that of Example 10, the above-titled compound (0.2 g) was obtained from the compound of Example 43 (0.30 g) and m-chloroperbenzoic acid (96 mg).

IR (KBr): $\gamma$ 3430, 2925, 2850, 1462, 1110, 1030, 950 cm$^{-1}$.

NMR (200 MHz, CDCl$_3$): $\delta$ 0.88(3H), 1.25(32H), 2.85–3.15(4H), 3.43(3H), 3.47(9H), 3.35–3.70(4H), 3.80–4.15(7H).

EXAMPLE 45

Production of 4-[3-[2-[2(2-methoxy-3-octadecyloxypropylthio)ethoxy]ethyl]imidazolio-1-yl]butyrate In the same manner as that of Example 43, the above-titled compound (0.49 g) was obtained from 2-[2-(2-methoxy-3-octadecyloxypropylthio)ethoxy]ethyl methanesulfonate (0.71 g) and ethyl 4-(imidazol-1-yl)butyrate.

IR (KBr): $\gamma$ 3425, 2925, 2852, 1570, 1462, 1395, 1158, 1115 cm$^{-1}$.

NMR (200 MHz,CDCl$_3$): $\delta$ 0.88(3H), 1.25(32H), 2.20(4H), 2.65–2.80(4H), 3.44(3H), 3.40–3.55(5H), 3.65(2H), 3.86(2H), 4.40(2H), 4.66(2H), 7.17(1H), 7.48(1H), 10.82(1H).

EXAMPLE 46

Production of 5-[1-[2-[2-(2-methoxy-3-octadecyloxypropylthio)ethoxy]ethyl]pyridinio-3-yl]-pentanoate In the same manner as that of Example 43, the above-titled compound (0.36 g) was obtained from 2-[2-(2-methoxy-3-octadecyloxypropylthio)ethoxy]ethyl methanesulfonate (0.72 g) and ethyl 5-(3-pyridin-3-yl)valerate (0.55 g).

IR (KBr): $\gamma$ 3440, 2925, 2850, 1720, 1630, 1560, 1502, 1462, 1410, 1110 cm$^{-1}$.

NMR (200 MHz,CDCl$_3$): $\delta$ 0.88(3H), 1.25(30H), 1.45–1.90(6H), 2.20(2H), 2.60–2.75(4H), 2.89(2H), 3.30–3.55(5H), 3.42(3H), 3.63(2H), 4.00(2H), 5.14(2H), 7.93(1H), 8.35(1H,d), 9.03(1H), 9.45(1H).

EXAMPLE 47

Production of N-[2-[2-[2-[3-octadecyloxy-2-(pyrimidin-2-yloxy)propylthio]ethoxy]ethoxy]ethyl]-N,N,N,trimethylammonium chloride In the same manner as that of Example 43, the above-titled compound (0.69 g) was obtained from the compound of Reference Example 37 (1.07 g).

IR (KBr): $\gamma$ 3425, 2925, 2850, 1630, 1475, 1460, 1362, 1420, 1310, 1120 cm$^{-1}$.

NMR (200 MHz,CDCl$_3$): $\delta$ 0.88(3H), 1.25(32H), 2.82(2H), 2.95(2H), 3.47(9H), 3.55–3.75(10), 3.99(4H), 5.40(1H), 6.99(1H), 8.53(2H).

EXAMPLE 48

Production of N-[2-[2-[3-octadecyloxy-2-(pyrimidin-2-yloxy)propylsulfinyl] ethoxy]ethoxy]ethyl-N,N,N-trimethylammonium chloride In the same manner as that of Example 43, the above-titled compound (0.26 g) was obtained from the compound of Reference Example 38 (1.0 g).

IR (KBr): $\gamma$ 3440, 2920, 2850, 1635, 1575, 1562, 1472, 1420, 1310, 1115, 1030 cm$^{-1}$.

NMR (200 MHz,CDCl$_3$): $\delta$ 0.88(3H), 1.25(32H), 2.90–4.15(18H), 3.44 & 3.46(9H), 5.75(1H), 7.03(1H), 8.55(2H).

EXAMPLE 49

Production of N-[2-[2-[4-octadecyloxy-3-(pyrimidin-2-yloxy)butylsulfinyl]ethoxy]ethyl]pyridinium chloride In the same manner as that of Example 2, the above-titled compound (659 mg) was obtained from the compound of Reference Example 47 (1.0 g).

IR (KBr): $\gamma$ 3440, 2925, 2860, 1630, 1580, 1562, 1490, 1465, 1425, 1320, 1120, 1102, 1020 cm$^{-1}$.

NMR (90 MHz,CDCl$_3$): $\delta$ 0.87(3H), 1.03–1.64(32H), 2.09–2.38(2H), 2.53–3.15(4H), 3.32–4.23(8H), 5.23–5.38(3H), 6.97(1H), 8.08(2H), 8.36–8.61(3H), 9.73(2).

EXAMPLE 50

Production of N-[2-[2-[4-octadecyloxy-3-(pyrimidin-2-yloxy)butylsulfinyl]ethoxy]ethyl]-N,N,N-trimethylammonium chloride In the same manner as that of Example 17, the above-titled compound (285 mg) was obtained from the compound of Reference Example 47 (0.80 g).

IR (KBr): $\gamma$ 3475, 3440, 2920, 2860, 1577, 1562, 1463, 1425, 1325, 1115, 1020 cm$^{-1}$.

NMR (200 MHz,CDCl$_3$): $\delta$ 0.88(3H), 1.25(30H), 1.52(2H), 2.10–2.42(2H), 2.77–3.06(4H), 3.32–4.75(4H), 3.48(9H,s), 3.90–4.20(6H), 5.35–5.53(1H), 6.98(1H), 8.54(2H).

EXAMPLE 51

Production of 1-[2-[2-(2-carboxymethoxy-3-octadecyloxypropylthiol)ethoxy]ethyl]-3-(4-carboxybutyl)pyridinium chloride The compound of Reference Example 52 (0.75 g) and ethyl 5-(pyridin-3-yl)valerate (0.50 g) were mixed, and the reaction was allowed to proceed at 80° C. for 8 hours. to the reaction mixture, after cooling, were added methanol (6 ml) and a 50% aqueous solution of sodium hydroxide (0.40 g). The mixture was stirred at room temperature overnight. The reaction mixture was adjusted to pH 3 with 1N hydrochloric acid, and dichloromethane (40 ml) was added, and then the mixture was washed with water and then with a saturated aqueous saline solution. The solvent was distilled off under reduced pressure. The residue was purified by means of a silica gel column chromatography [carrier; 30 g, developing solvent; chloroform:methanol:water=65:25:4] to obtain the above-titled compound (0.59 g).

IR (KBr): $\gamma$3450, 2925, 2860, 1725, 1630, 1465, 1215, 1115, 720 cm$^{-1}$.

NMR (200 MHz,CDCl$_3$-CD$_3$OD): $\delta$ 0.88(3H), 1.26(30H), 1.46–1.87(6), 2.69–2.74(4H), 2.90(2H)), 3.39–3.70(7H), 3.97–4.23(4H), 4.90–5.00(2H), 7.97(1H), 8.28(1H), 9.00(1H), 9.09(1H).

EXAMPLE 52

Production of 1-[2-[2-[3-(6-pentylnaphthalen-2-yl)-propyloxy-2-(pyrimidin-2-yloxy)propylsulfinyl]ethoxy]-ethyl]pyridinium chloride In the same manner as that of Example 2, the above-titled compound (0.40 g) was obtained from the compound of Reference Example 57 (0.90 g) and pyridine (5 ml).

IR (Neat): $\gamma$ 3425, 3050, 2960, 2930, 2870, 1630, 1575, 1565, 1490, 1420, 1315, 1120, 1040, 810, 680 cm$^{-1}$.

NMR (200 MHz,CDCl$_3$): $\delta$ 0.89(3H), 1.26–1.40(4H), 1.63–1.75(2H), 1.88–2.00(2H), 2.70–3.30(8H), 3.47–3.56(2H), 3.70–4.23(6H), 5.24–5.34(2H), 5.72(1H), 7.02(1H), 7.23–7.28(2H), 7.55(2H), 7.68(2H), 7.95(2H), 8.30(1H), 8.55(2H), 9.61(2H).

EXAMPLE 53

Production of N-[2-[2-[2-[3-octadecyloxy-2-(pyrimidin-2-yloxy)propylsulfinyl]ethylsulfinyl]ethoxy]ethyl]-pyridinium chloride In the same manner as that of Example 2, a crude product of N-[2-[2-[2-[3-octadecyloxy-2-(pyrimidin-2-yloxy)propylthio]ethoxy]ethyl]pyridinium chloride was obtained from the compound of Reference Example 61 (635 mg) and pyridine (3 ml). The whole amount of this crude product was, in the same manner as that of Reference Example 4, subjected to oxidation with m-chloroperbenzoic acid (420 mg) to give the above-titled compound (340 mg).

IR (Nujol): $\gamma$ 3370, 1575, 1565, 1485, 1420, 1375, 1310, 1115, 1100, 1015 cm$^{-1}$.

NMR (90 MHz,CDCl$_3$-Cd$_3$OD): $\delta$ 0.87(3H), 1.27(32H), 2.70–3.57(10H), 3.73–4.17(6H), 5.07(2H), 5.77(1H), 7.03(1H), 8.10(2H), 8.47(1H), 8.57(2H), 9.33(2H).

EXAMPLE 54

Production of N-[2-[2-[3-octadecyloxy-2-(pyrimidin-2-yloxy)propylsulfinyl]ethylsulfinyl]ethoxy]ethyl]-N,N,N-trimethylammonium chloride In the same manner as that of Example 17, the above-titled compound (220 mg) was obtained from the compound of Reference Example 62 (450 mg).

IR (Nujol): $\gamma$ 3380, 1575, 1420, 1370, 1310, 1110, 1020 cm$^{-1}$.

NMR (90 MHz,CDCl$_3$-CDC$_3$OD): $\delta$ 0.87(3H), 1.23(3H), 2.97–3.57(19H), 3.73–4.10(8H), 5.70(1H), 7.03(1H), 8.57(2H).

What is claimed is:

1. A compound represented by the formula:

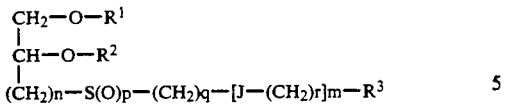

wherein R¹ stands for an alkyl group having 8 to 20 carbon atoms which may be substituted by phenyl, naphthyl, $C_{3-8}$ cycloalkyl, $C_{1-6}$ alkyl, vinyl, ethynyl, hydroxy, $C_{1-6}$ alkoxy, halogen or oxo; or may contain phenyl, naphthyl, $C_{3-8}$ cycloalkyl, vinyl or ethynyl as a divalent group;

R² stands for an alkyl group having 1 to 6 carbon atoms or a nitrogen-containing heterocyclic group selected from the class consisting of pyrrolyl, imidazolyl, pyrazolyl, oxazolyl, isooxazolyl, thiazolyl, 1,2,3-oxadiazolyl, triazolyl, tetrazolyl, thiadiazolyl, piperidinyl, N-methylpiperazinyl, N-ethylpiperazinyl, morpholinyl, thiomorpholinyl, pyridyl, pyridazinyl, pyrimidinyl, pyrazinyl, triazinyl, benzoxazolyl, benzothiazolyl, isoindolyl, indolyl, indolizinyl, indazolyl, purinyl, quinolyl, isoquinolyl, quinolidinyl, phthalazinyl, quinoxalinyl, quinazolinyl, cinnolinyl and pteridinyl;

R³ stands for (i) a tertiary amino group represented by the formula:

wherein R⁴ and R⁵ respectively stand for an alkyl group having 1 to 6 carbon atoms, or R⁴ and R⁵, taken together with the adjacent nitrogen atom, form a cyclic amino group selected from the class consisting of 1-pyrrolyl, 1-pyrazolyl, 1-imidazolyl, piperidino, 1,4-dihydropyridin-1-yl, 1-piperazinyl, 1-($C_{1-6}$ alkyl)piperazin-4yl, morpholino, thiomorpholino, 1-indolyl, 1-indolinyl, 2-isoindolyl and 2-isoindolinyl, (ii) a heterocyclic group containing a tertiary nitrogen atom selected from the class consisting of 1-($C_{1-6}$ alkyl)pyrrolidin-(2 or 3)-yl, 1-($C_{1-6}$ alkyl)pyrrolin-(2 or 3)-yl, 1-($C_{1-6}$ alkyl)pyrrol-(2 or 3)-yl, 1-($C_{1-6}$ alkyl)imidazolin-(2 or 4)-yl, 1-($C_{1-6}$ alkyl)-imidazol-(2 or 4)-yl, 1-($C_{1-6}$ alkyl)-pyrazolin-(3, 4 or 5)-yl, 1-($C_{1-6}$ alkyl)pyrazol-(3, 4 or 5)-yl, oxazol-(2, 4 or 5)-yl, thiazol-(2, 4 or 5)-yl, 1-($C_{1-6}$ alkyl)piperidin-(2, 3 or 4)-yl, pyridin-(2, 3 or 4)-yl, pyrimidin-(2, 4, 5 or 6)-yl, pyridazin-(3 or 4)-yl, pyrazin-(2 or 3)-yl, 1-($C_{1-6}$ alkyl)piperazin-(2 or 3)-yl), 4-($C_{1-6}$ alkyl)morpholin-(2 or 3)-yl, 4-($C_{1-6}$ alkyl)-thiomorpholin-(2 benzothiazol-(2, 4, 5, 6 or 7)-yl, 2-($C_{1-6}$ alkyl)isoindolyl, 1-($C_{1-6}$ alikyl)indolyl, 7-($C_{1-6}$ alkyl)purinyl, isoquinolinyl, quinolinyl, phthalazinyl, quinoxalinyl, quinazolinyl, cinnolinyl and pteridinyl, (III) a quaternary ammonium group represented by the formula:

wherein R⁴, R⁵ and R⁶ respectively stand for an alkyl group having 1 to 6 carbon atoms, or R⁴, R⁵ and R⁶, taken together with the adjacent nitrogen atom, form a cyclic ammonium group selected from the class consisting of 1-pyridinio, 3-oxazolio, 3-thiazolio, 1-imidazolio, 1-pyrazinio, 1-pyrimidinio, 1-pyridazinio, 4-indolizinio, benzoxazolio, benzothiazolio, 1-quinolinio, 2-isoquinolinio, 2-phthalazinio, 1-quinoxalinio, 1- or 3-quinazolinio, 1- or 2-cinnolinio, 1-, 3-, 5- or 8-pteridinio, 1-($C_{1-6}$ alkyl)-1-pyrrolinio, 1-($C_{1-6}$ alkyl)-1-pyrrolidinio, 1-($C_{1-6}$ alkyl)-3-imidazolio, 1-($C_{1-6}$ alkyl))-3-imidazolinio, 1-($C_{1-6}$ alkyl)-2-pyrazolio, 1-($C_{1-6}$ alkyl)-1-piperidinio, 1-($C_{1-6}$ alkyl)-1-piperazinio, 4-($C_{1-6}$ alkyl)-4-morpholinio, 4-($C_{1-6}$ alkyl)-4-thiomorpholinio, 1-($C_{1-6}$ alkyl)-1-indolinio and 2-($C_{1-6}$ alkyl)-2-isoindolinio, or (iv) a heterocyclic group containing a quaternary nitrogen atom selected from the class consisting of 1,1-di($C_{1-6}$ alkyl)-pyrrolidinio-(2 or 3)-yl, 1,1-di($C_{1-6}$ alkyl)pyrrolinio-(2 or 3)-yl, 1,3-di($C_{1-6}$ alkyl)imidazoliol-(2, 3 or 4)-yl, 1,3-di($C_{1-6}$ alkyl)imidazolinio-(2, 3 or 4)-yl, 3-($C_{1-6}$ alkyl)oxazolio-(2, 4 or 5)-yl, 3-($C_{1-6}$ alkyl)thiazolio-(2, 4 or 5)-yl, 1-($C_{1-6}$ alkyl)pyridinio-(2, 3 or 4)-yl, 1,1-di($C_{1-6}$ alkyl)piperidinio-(2, 3 or 4)-yl, 1,1-di($C_{1-6}$ alkyl)piperazinio-(2 or 3)-yl, 1-($C_{1-6}$ alkyl)-pyrazinio-(2 or 3)-yl, 1-($C_{1-6}$ alkyl)pyrimidiniol-(2, 4, 5 or 6)-yl, 1-($C_{1-6}$ alkyl)pyridazinio-(3 or 4)-yl, 4,4-di($C_{1-6}$ alkyl)morpholinio-(2 or 3)-yl, 4,4-di($C_{1-6}$ alkyl)-thiomorpholinio-(2 or 3)-yl, 1-($C_{1-6}$ alkyl)-benzoxazolio-(2, 4, 5, 6 or 7)-yl, 1-($C_{1-6}$ alkyl)benzothiazolio-(2, 4, 5, 6 or 7)yl, 1-($C_{1-6}$ alkyl)quinolinio-(2, 3, 4, 5, 6, 7 or 8)-yl and 1,1,4-tri($C_{1-6}$ alkyl)-piperazinio-(2 or 3)-yl;

each J stands for an oxygen atom or $S(O)_t$ where t denotes 0, 1 or 2;

m denotes 1 or 2 n denotes 1 or 2 p denotes 0, 1 or 2 q denotes an integer of 2 to 5;

each r denotes an integer of 2 to 5; and each of said alkyl groups represented by R², R⁴, R⁵ and R⁶, said nitrogen-containing heterocyclic group represented by R², said cyclic amino group formed by R⁴, R⁵ and the adjacent nitrogen atom, said heterocyclic group containing a tertiary nitrogen atom, said cyclic ammonium group formed by R⁴, R⁵, R⁶ and the adjacent nitrogen atom and said heterocyclic group containing a quaternary nitrogen atom being unsubstituted or substituted by halogen, $C_{1-6}$ alkyl, $C_{2-6}$ alkenyl, $C_{3-6}$ cycloalkyl, $C_{5-6}$ cycloalkenyl, phenyl-$C_{1-6}$ alkyl, phenyl, $C_{1-6}$ alkylthio, $C_{1-6}$ alkylsulfinyl, phenylsulfinyl, $C_{1-6}$ alkylsulfonyl, phenylsulfonyl, mercapto, sulfino, sulfo, phosphono, sulfamoyl, N-$C_{1-6}$ alkylsulfamoyl, N,N-di-$C_{1-6}$ alkylsulfamoyl, 3- to 6-membered cyclic aminosulfonyl selected from the class consisting of 1-pyrrolidinylsulfonyl, 1-piperidinylsulfonyl, 1-piperazinylsulfonyl, 1-methylpiperazin-4-ylsulfonyl and morpholinosulfonyl, imino, amidino, amino, N-$C_{1-6}$ alkylamino, N,N-di-$C_{1-6}$ alkylamino, 3- to 6-membered cyclic amino selected from the class consisting of 1-azetidinyl, 1-pyrrolidinyl, 1-piperidinyl, 1-piperazinyl, 1-methylpiperazin-4-yl and morpholino, N,N,N-tri-$C_{1-6}$ alkylammonium, $C_{1-6}$ alkanoyl, $C_{1-6}$ alkanoylamino, benzamido, benzoyl, $C_{1-6}$ alkanoyloxy, benzoyloxy, $C_{1-6}$ alkoxy, $C_{2-7}$ alkoxycarbonyl, phenoxy, phenylthio, hydroxy, oxo, thioxo, epoxy, hydroxy-$C_{1-6}$ alkyl, aminol-$C_{1-6}$ alkyl, N-$C_{1-6}$ alkylaminol-$C_{1-6}$ alkyl, N,N-di-$C_{1-6}$ alkylamino-$C_{1-6}$ alkyl, 3- to 6-membered cyclic aminol-$B_{1-6}$ alkyl in which the 3- to 6-membered cyclic amino moiety is selected from the class consisting of 1azetidinyl, 1-pyrrolidinyl, 1-piperidinyl, 1-piuperazinyl, 1-methylpiperazin-4-yl and morpholino, N,N,N-tri-$C_{1-6}$ alkylammoniol-$C_{1-6}$ alkyl, carboxyl, carboxy-$C_{1-6}$ alkyl, carbamoyl, N-$C_{1-6}$ alkylcarbamoyl, N,N-di-$C_{1-6}$ alkylcarbamoyl, 3- to 6-membered cyclic aminocarbonyl selected from the class consisting of 1-azetidinylcarbonyl, 1-pyrrolidinylcarbonyl, 1-piperidinylcarbonyl, 1-piperazinylcarbonyl, 1-methylpiperazinl-4-ylcarbonyl and morpholinocarbonyl, cyano, trifluoromethyl or ureido; or a pharmaceutically acceptable salt thereof with the proviso that at least one of $R^2$ and $R^3$ heterocyclic.

2. A compound according to claim 1 or a salt thereof, wherein $R^3$ stands for a group represented by the formula:

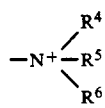

wherein $R^4$, $R^5$ and $R^6$, taken together with the adjacent nitrogen atom, form a cyclic ammonium group selected from the class consisting of 1-pyridinio, 3-oxazolio, 3-thiazolio, 1-imidazolio, 1-pyrazinio, 1-pyrimidinio, 1-pyridazinio, 4-indolizinio, benzoxazolio, benzothiazolio, 1-quinolinio, 2-isoquinolinio, 2-phthalazinio, 1-quinoxalinio, 1- or 3-quinazolinio, 1- or 2-cinnolinio, 1-, 3-, 5- or 8-pteridinio, 1-($C_{1-6}$ alkyl)-1-pyrrolinio, 1-($C_{1-6}$ alkyl)-1-pyrrolidinio, 1-($C_{1-6}$ alkyl)-3-imidazolio, 1($C_{1-6}$ alkyl)-3-imidazolinio, 1-($C_{1-6}$ alkyl)-2-pyrazolio, 1-($C_{1-6}$ alkyl)-1-piperidinio, 1-($C_{1-6}$ alkyl)-1-piperazinio, 4-($C_{1-6}$ alkyl)-4-morpholinio, 4-($C_{1-6}$ alkyl)-4-thiomorpholinio, 1-($C_{1-6}$ alkyl)-1-indolinio and 2-($C_{1-6}$ alkyl)-2-isoindolinio, each of said groups being unsubstituted or substituted by halogen, $C_{1-6}$ alkyl, $C_{2-6}$ alkenyl, $C_{3\neq}$cycloalkyl, $C_{5-6}$ cycloalkenyl, phenyl-$C_{1-6}$ alkyl, phenyl, $C_{1-6}$ alkylthio, $C_{1-6}$ alkylsulfinyl, phenylsulfinyl, $C_{1-6}$ alkylsulfonyl, phenylsulfonyl, mercapto, sulfino, sulfo, phosphono, sulfamoyl, N-$C_{1-6}$ alkylsulfamoyl, N,N-di-$C_{1-6}$ alkylsulfamoyl, 3- to 6-membered cyclic aminosulfonyl selected from the class consisting of 1-pyrrolidinylsulfonyl, 1-piperidinylsulfonyl, 1-piperazinylsulfonyl, 1-methylpiperazin-4-ylsulfonyl and morpholinosulfonyl, imino, amidino, amino, N-$C_{1-6}$ alkylamino, N,N-di-$C_{1-6}$ alkylamino, 3- to 6-membered cyclic amino selected from the class consisting of 1-azetidinyl, 1-pyrrolidinyl, 1-piperidinyl, 1-piperazinyl, 1-methylpiperazin-4-yl and morpholino, N,N,N-tri-$C_{1-6}$ alkylammonium, $C_{1-6}$ alkanoyl, $C_{1-6}$ alkanoyamino, benzamido, benzoyl, $C_{1-6}$ alkanoyloxy, benzoyloxy, $C_{1-6}$ alkoxy, $C_{2-7}$ alkoxycarbonyl, phenoxy, phenylthio, hydroxy, oxo, thioxo, epoxy, hydroxy-$C_{1-6}$ alkyl, amino-$C_{1-6}$ alkyl, N-$C_{1-6}$ alkylamino-$C_{1-6}$ alkyl, N,N-di-$C_{1-6}$ alkylamino-$C_{1-6}$ alkyl, 3- to 6-membered cyclic amino-$C_{1-6}$ alkyl in which the 3- to 6-membered cyclic amino moiety is selected from the class consisting of 1-azetidinyl, 1-pyrrolidinyl, 1-piperidinyl, 1-piperazinyl, 1-methylpiperazin-4-yl and morpholino, N,N,N-tri-$C_{1-6}$ alkylammonio-$C_{1-6}$ alkyl, carboxyl, carboxy-$C_{1-6}$ alkyl, carbamoyl, N-$C_{1-6}$ alkylcarbamoyl, N,N-di-$C_{1-6}$ alkylcarbamoyl, 13- to 6-membered cyclic aminocarbonyl selected from the class consisting of 1-azetidinylcarbonyl, 1-pyrrolidinylcarbonyl, 1-piperidinylcarbonyl, 1-piperazinylcarbonyl, 1-methylpiperazinl-4-ylcarbonyl and morpholinocarbonyl, cyano, trifluoromethyl or ureido.

3. A compound according to claim 1 or a salt thereof, wherein $R^1$ stands for an alkyl group having 8 to 20 carbon atoms.

4. A compound according to claim 1 or a salt thereof, wherein $R^1$ stands for an n-octadecyl group.

5. A compound according to claim 1 or a salt thereof, wherein $R^2$ stands for a pyrimidinyl group.

6. A compound according to claim 1 or a salt thereof, wherein $R^3$ stands for a 1-pyridinio group.

7. A compound according to claim 1 or a salt thereof, wherein J stands for an oxygen atom.

8. A compound according to claim 1 or a salt thereof, wherein m denotes 1.

9. A compound according to claim 1 or a salt thereof, wherein n denotes 1.

10. A compound according to claim 1 or a salt thereof, wherein p denotes 1.

11. A compound according to claim 1 or a salt thereof, wherein q and r denote 2.

12. A salt according to claim 1, which is 2-[2-[3-octadecyloxy-2-(pyrimidin-2-yloxy)propylsulfinyl]ethoxyethylthiazolium chloride.

13. A salt according to claim 1, which is N-[2-[2-[3-octadecyloxy-2-(pyrimidin-2-yloxy)propylsulfinyl]ethoxy]ethyl]pyridinium chloride.

14. A salt according to claim 1, which is 3-(3-hydroxypropyl)-1-[2-[2-[3-octadecyloxy-2-(pyrimidin-2-yloxy)propylsulfinyl]ethoxy]ethyl]pyridinium chloride.

15. A salt according to claim 1, which is 3-(3-hydroxypropyl)-4-methyl-3-[2-[2-[3-octadecyloxy-2-(pyrimidin-2-yloxy)propylsulfinyl]ethoxy]ethyl]thiazolium chloride.

16. A salt according to claim 1, which is 6-[3-[2-[2-[3-octadecyloxy-2-(pyrimidin-2-yloxy)propysulfinyl]ethoxy]-ethyl]imidazolio-1-yl]hexanoate.

17. A compound represented by the formula:

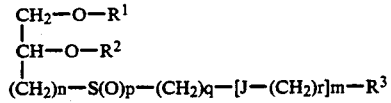

wherein $R^1$ stands for an alkyl group having 8 to 20 carbon atoms which may be substituted by phenyl, naphthyl, $C_{3-8}$ cycloalkyl, $C_{1-6}$ alkyl, vinyl, ethynyl, hydroxy, $C_{1-6}$ alkoxy, halogen or oxo; or may contain phenyl, naphthyl, $C_{3-8}$ cycloalkyl, vinyl or ethynyl as a divalent group;

$R^2$ stands for an alkyl group having 1 to 6 carbon atoms or a pyrimidinyl group;

$R^3$ stands for (i) a tertiary amino group represented by the formula:

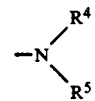

wherein R⁴ and R⁵ respectively stand for an alkyl group having 1 to 6 carbon atoms, or R⁴ and R⁵, taken together with the adjacent nitrogen atom, form a cyclic amino group selected from the class consisting of 1-pyrrolyl, 1-pyrazolyl, 1-imidazolyl, piperidino, 1,4-dihydropyridin-1-yl, 1-piperazinyl, 1-($C_{1-6}$ alkyl)piperazin-4-yl, morpholino, thiomorpholino, 1-indolyl, 1-indolinyl, 2-isoindolyl and 2-isoindolinyl, (ii) a heterocyclic group containing a tertiary nitrogen atom selected from the class consisting of 1-($C_{1-6}$ alkyl)pyrrolidin-(2 or 3)-yl, 1-($C_{1-6}$ alkyl)pyrrolin-(2 or 3)-yl, 1-($C_{1-6}$ alkyl)pyrrol-(2 or 3)-yl, 1-($C_{1-6}$ alkyl)imidazolin-(2 or 4)-yl, 1-($C_{1-6}$ alkyl)-imidazol-(2 or 4)-yl, 1-($C_{1-6}$ alkyl)-pyrazolin-(3, 4 or 5)-yl, 1-($C_{1-6}$ alkyl)yrazol-(3, 4 or 5)-yl, oxazol-(2, 4 or 5)-yl, thiazol-(2, 4 or 5)-yl, 1-($C_{1-6}$ alkyl)piperidin-(2, 3 or 4)-yl, pyridin-(2, 3 or 4)-yl, pyrimidin-(2, 4, 5 or 6)-yl, pyridazin-(3 or 4)-yl, pyrazin-(2 or 3)-yl, 1-($C_{1-6}$ alkyl)piperazin-(2 or 3)-yl, 4-($C_{1-6}$ alkyl)morpholin-(2 or 3)-yl, 4-($C_{1-6}$ alkyl)-thiomorpholin-(2 or 3)-yl, benzoxazol-(2, 4, 5, 6 or 7)-yl, benzothiazol-(2, 4, 5, 6 or 7)-yl, 2-($C_{1-6}$ alkyl)isoindolyl, 1-($C_{1-6}$ alkyl)indolyl, 7-($C_{1-6}$ alkyl)purinyl, isoquinolinyl, quinolinyl, phthalazinyl, quinoxalinyl, quinazolinyl, cinnolinyl and pteridinyl, (iii) a quaternary ammonium group represented by the formula:

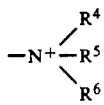

wherein R⁴, R⁵ and R⁶ respectively stand for an alkyl group having 1 to 6 carbon atoms, or R⁴, R⁵ and R⁶, taken together with the adjacent nitrogen atom, form a cyclic ammonium group selected from the class consisting of 1-pyridinio, 3-oxazolio, 3-thiazolio, 1-imidazolio, 1-pyrazinio, 1-pyrimidinio, 1-pyridazinio, 4-indolizinio, benzoxazolio, benzothiazolio, 1-quinolinio, 2-isoquinolinio, 2-phthalazinio, 1-quinoxalinio, 1- or 3-quinazolinio, 1- or 2-cinnolinio, 1-, 3-, 5- or 8-pteridinio, 1-($C_{1-6}$ alkyl)-1-pyrrolinio, 1-($C_{1-6}$ alkyl)-1-pyrrolidinio, 1-($C_{1-6}$ alkyl)-3-imidazolio, 1-($C_{1-6}$ alkyl)-3-imidazolinio, 1-($C_{1-6}$ alkyl)-2-pyrazolio, 1-($C_{1-6}$ alkyl)-1-piperidinio, 1-($C_{1-6}$ alkyl)-1-piperazinio, 4-($C_{1-6}$ alkyl)-4-morpholinio, 4-($C_{1-6}$ alkyl)-4-thiomorpholinio, 1-($C_{1-6}$ alkyl)-1-indolinio and 2-($C_{1-6}$ alkyl)-2-isoindolinio, or (iv) a heterocyclic group containing a quaternary nitrogen atom selected from the class consisting of 1,1-di($C_{1-6}$ alkyl)-pyrrolidinio-(2 or 3)-yl, 1,1-di($C_{1-6}$ alkyl)pyrrolinio-(2 or 3)-yl, 1,3-di($C_{1-6}$ alkyl)imidazolio-(2, 3 or 4)-yl, 1,3-di($C_{1-6}$ alkyl)imidazolinio-(2, 3 or 4)-yl, 3-($C_{1-6}$ alkyl)oxazolio-(2, 4 or 5)-yl, 3-($C_{1-6}$ alkyl)thiazolio-(2, 4 or 5)-yl, 1-($C_{1-6}$ alkyl)pyridinio-(2, 3 or 4)-yl, 1,1-di($C_{1-6}$ alkyl)piperidinio(2, 3 or 4)-yl, 1,1-di($C_{1-6}$ alkyl)piperazinio-(2 or 3)-yl, 1-($C_{1-6}$ alkyl)pyrazinio-(2 or 3)-yl, 1-($C_{1-6}$ alkyl)pyrimidinio-(2, 4, 5 or 6)-yl, 1-($C_{1-6}$ alkyl)pyridaziniol-(3 or 4)-yl, 4,4-di($C_{1-6}$ alkyl)morpholiniol-(2 or 3)-yl, 4,4-di($C_{1-6}$ alkyl)-thiomorpholinio-(2 or 3)-yl, 1-($C_{1-6}$ alkyl)-benzoxazoliol-(2, 4, 5, 6 or 7)-yl, 1-($C_{1-6}$ alkyl)benzothiazolio-(2, 4, 5, 6 or 7)-yl, 1-($C_{1-6}$ alkyl)quinolinio-(2, 3, 4, 5, 6 or 8)-yl, 2-($C_{1-6}$ alkyl)isoquinolinio-(1, 3, 4, 5, 6, 7 or 8)-yl and 1,1,4-tri($C_{1-6}$ alkyl piperazinio-(2 or 3)-yl;

each J stands for an oxygen atom or S(O)t where t denotes 0, 1 or 2;

m denotes 1 or 2;

n denotes 1 or 2;

p denotes 0, 1 or 2;

q denotes an integer of 2 to 5;

each r denotes an integer of 2 to 5; and each of said alkyl groups represented by R², R⁴, R⁵ and R⁶, said pyrimidinyl group represented by R², said cyclic amino group formed by R⁴, R⁵ and the adjacent nitrogen atom, said heterocyclic group containing a tertiary nitrogen atom, said cyclic ammonium group formed by R⁴, R⁵, R⁶ and the adjacent nitrogen atom and said heterocyclic group containing a quaternary nitrogen atom being unsubstituted or substituted by halogen, $C_{1-6}$ alkyl, $C_{2-6}$ alkenyl, $C_{3-6}$ cycloalkyl, $C_{5-6}$ cycloalkenyl, phenyl-$C_{1-6}$ alkyl, phenyl, $C_{1-6}$ alkylthio, $C_{1-6}$ alkylsulfinyl, phenylsulfinyl, $C_{1-6}$ alkylsulfonyl, phenylsulfonyl, mercapto, sulfino, sulfo, phosphono, sulfamoyl, N-$C_{1-6}$ alkylsulfamoyl, N,N-di-$C_{1-6}$ alkylsulfamoyl, 3- to 6-membered cyclic aminosulfonyl selected from the class consisting of 1-pyrrolidinyl sulfonyl, 1-piperidinyl sulfonyl, 1-piperazinylsulfonyl, 1-methylpiperazin-4-ylsulfonyl and morpholinosulfonyl, imino, amidino, amino, N-$C_{1-6}$ alkylamino, N,N-di-$C_{1-6}$ alkylamino, 3- to 6-membered cyclic amino selected from the class consisting of 1-azetidinyl, 1-pyrrolidinyl, 1-piperidinyl, 1-piperazinyl, 1-methylpiperazin-4-yl and morpholino, N,N,N-tri-$C_{1-6}$ alkylammonium, $C_{1-6}$ alkanoyl, $C_{1-6}$ alkanoylamino, benzamido, benzoyl, $C_{1-6}$ alkanoyloxy, benzoyloxy, $C_{1-6}$ alkoxy, $C_{2-7}$ alkoxycarbonyl, phenoxy, phenylthio, hydroxy, oxo, thioxo, epoxy, hydroxy-$C_{1-6}$ alkyl, amino-$C_{1-6}$ alkyl, N-$C_{1-6}$ alkylamino-$C_{1-6}$ alkyl, N,N-di-$C_{1-6}$ alkylamino-$C_{1-6}$ alkyl, 3- to 6-membered cyclic amino-$C_{1-6}$ alkyl in which the 3- to 6-membered cyclic amino moiety is selected from the class consisting of 1-azetidinyl, 1-pyrrolidinyl, 1-piperidinyl, 1-piperazinyl, 1-methylpiperazin-4yl and morpholino, N,N,N-tri-$C_{1-6}$ alkylammonio-$C_{1-6}$ alkyl, carboxyl, carboxy-$C_{1-6}$ alkyl, carbamoyl, N-$C_{1-6}$ alkylcarbamoyl, N,N-di-$C_{1-6}$ alkylcarbamoyl, 3- to 6-membered cyclic aminocarbonyl selected from the class consisting of 1-azetidinylcarbonyl, 1-pyrrolidinylcarbonyl, 1-piperidinylcarbonyl, 1-piperazinylcarbonyl, 1-methylpiperazin-4-ylcarbonyl and morpholinocarbonyl, cyano, trifluoromethyl or ureido; or a pharmaceutically acceptable salt thereof with the proviso that at least one of R² and R³ heterocyclic.

18. A compound according to claim 17 or a salt thereof, wherein R¹ stands for an alkyl group having 8 to 20 carbon atoms.

19. A compound according to claim 17 or a salt thereof, wherein R¹ stands for an n-octadecyl group.

20. A compound according to claim 17 or a salt thereof, wherein R² stands for a pyrimidinyl group.

21. A compound according to claim 17 or a salt thereof, wherein R³ stands for a group represented by the formula:

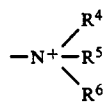

wherein R⁴, R⁵ and R⁶, taken together with the adjacent nitrogen atom, form a cyclic ammonium group selected from the class consisting of 1-pyridinio, 3-oxazolio, 3-thiazolio, 1-imidazolio, 1-pyrazinio, 1-pyrimidinio, 1-pyridazinio, 4-indolizinio, benzoxazolio, benzothiazolio, 1-quinolinio, 2-isoquinolinio, 2-phthalazinio, 1-quinoxalinio, 1- or 3-quinazolinio, 1- or 2-cinnolinio, 1-, 3-, 5- or 8-pteridinio, 1-($C_{1-6}$ alkyl)-1-pyrrolinio, 1-($C_{1-6}$ alkyl)-1-pyrrolidinio, 1-($C_{1-6}$ alkyl)-3-imidazolio, 1-($c_{1-6}$ alkyl)-3-imidazolinio, 1-($c_{1-6}$ alkyl)-2-pyrazolio, 1-($C_{1-6}$ alkyl)-1-piperidinio, 1-($C_{1-6}$ alkyl)-1-piperazinio, 4-($C_{1-6}$ alkyl)-4-morpholinio, 4-($C_{1-6}$ alkyl)-4-thiomorpholinio, 1-($C_{1-6}$ alkyl)-1-indolinio and 2-($C_{1-6}$ alkyl)-2-isoindolinio, each of said groups being unsubstituted or substituted by halogen, $C_{1-6}$ alkyl, $C_{2-6}$ alkenyl, $C_{3-6}$ cycloalkyl, $C_{5-6}$ cycloalkenyl, phenyl-$C_{1-6}$ alkyl, phenyl, $C_{1-6}$ alkylthio, $C_{1-6}$ alkylsulfinyl, phenylsulfinyl, $C_{1-6}$ alkylsulfonyl, phenylsulfonyl, mercapto, sulfino, sulfo, phosphono, sulfamoyl, N-$C_{1-6}$ alkylsulfamoyl, N,N-di-$C_{1-6}$ alkylsulfamoyl, 3- to 6-membered cyclic aminosulfonyl selected from the class consisting of 1-pyrrolidinylsulfonyl, 1-piperidinylsulfonyl, 1-piperazinylsulfonyl, 1-methylpiperazin-4-ylsulfonyl and morpholinosulfonyl, imino, amidino, amino, N-$C_{1-6}$ alkylamino, N,N-di-$C_{1-6}$ alkylamino, 3- to 6-membered cyclic amino selected from the class consisting of 1-azetidinyl, 1-pyrrolidinyl, 1-piperidinyl, 1-piperazinyl, 1-methylpiperazin-4-yl and morpholino, N,N,N-tri-$C_{1-6}$ alkylammonium, $C_{1-6}$ alkanoyl, $C_{1-6}$ alkanoylamino, benzamido, benzoyl, $C_{1-6}$ alkanoyloxy, benzoyloxy, $C_{1-6}$ alkoxy, $C_{2-7}$ alkoxycarbonyl, phenoxy, phenylthio, hydroxy, oxo, thioxo, epoxy, hydroxy-$C_{1-6}$ alkyl, amino-$C_{1-6}$ alkyl, N-$C_{1-6}$ alkylaminol-$C_{1-6}$ alkyl, N,N-di-$C_{1-6}$ alkylamino-$C_{1-6}$ alkyl, 3- to 6-membered cyclic amino-$C_{1-6}$ alkyl in which the 3- to 6-membered cyclic amino moiety is selected from the class consisting of 1-azetidinyl, 1-pyrrolidinyl, 1-piperidinyl, 1-piperazinyl, 1-methylpiperazin-4-yl and morpholino, N,N,N-tri-$C_{1-6}$ alkylammonio-$C_{1-6}$ alkyl, carboxyl, carboxy-$C_{1-6}$ alkyl, carbamoyl, N-$C_{1-6}$ alkylcarbamoyl, N,N-di-$C_{1-6}$ alkylcarbamoyl, 3- to 6-membered cyclic aminocarbonyl selected from the class consisting of 1-azetidinylcarbonyl, 1-pyrrolidinylcarbonyl, 1-piperidinylcarbonyl, 1-piperazinylcarbonyl, 1-methylpiperazin-4-ylcarbonyl and morpholinocarbonyl, cyano, trifluoromethyl or ureido.

22. A compound according to claim 17 or a salt thereof, wherein $R^3$ stands for a 1-pyridinio group.

23. A compound according to claim 17 or a salt thereof, wherein J stands for an oxygen atom.

24. A compound according to claim 17 or a salt thereof, wherein p denotes 1.

25. A compound according to claim 17 or a salt thereof, wherein q and r denote 2.

26. A compound according to claim 17 or a salt thereof, wherein m and n denote 1 and J stands for an oxygen atom.

27. A compound according to claim 17, which is represented by the formula:

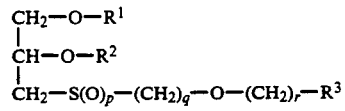

wherein $R^1$ stands for an alkyl group having 8 to 20 carbon atoms which may be substituted by phenyl, naphthyl, $C_{3-8}$ cycloalkyl, $C_{1-6}$ alkyl, vinyl, ethynyl, hydroxy, $C_{1-6}$ alkoxy, halogen or oxo; or may contain phenyl, naphthyl, $C_{3-8}$ cycloalkyl, vinyl or ethynyl as a divalent group;

$R^2$ stands for a pyrimidinyl group;

$R^3$ stands for a quaternary ammonium group represented by the formula:

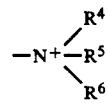

wherein R⁴, R⁵ and R⁶, taken together with the adjacent nitrogen atom, form a cyclic ammonium group selected from the class consisting of 1-pyridinio, 3-oxazolio, 3-thiazolio, 1-imidazolio, 1-pyrazinio, 1-pyrimidinio, 1-pyridazinio, 4-indolizinio, benzoxazolio, benzothiazolio, 1-quinolinio, 2-isoquinolinio, 2-phthalazinio, 1-quinoxalinio, 1- or 3-quinazolinio, 1- or 2-cinnolinio, 1-, 3-, 5- or 8-pteridinio, 1-($C_{1-6}$ alkyl)-1-pyrrolinio, 1-($C_{1-6}$ alkyl)-1-pyrrolidinio, 1-($C_{1-6}$ alkyl)-3-imidazolio, 1-($C_{1-6}$ alkyl)-3-imidazolinio, 1-($C_{1-6}$ alkyl)-2-pyrazolio, 1-($C_{1-6}$ alkyl)-1-piperidinio, 1-($C_{1-6}$ alkyl)-1-piperazinio, 4-($C_{1-6}$ alkyl)-4-morpholinio, 4-($C_{1-6}$ alkyl)-4-thiomorpholinio, 1-($C_{1-6}$ alkyl)-1-indolinio and 2-($C_{1-6}$ alkyl)-2-isoindolinio;

p denotes 0, 1 or 2;

q denotes an integer of 2 to 5;

r denotes an integer of 2 to 5; and said quaternary ammonium group represented by $R^3$ being unsubstituted or substituted by halogen, $C_{1-6}$ alkyl, $C_{2-6}$ alkenyl, $C_{3-6}$ cycloalkyl, $C_{5-6}$ cycloalkenyl, phenyl-$C_{1-6}$ alkyl, phenyl, $C_{1-6}$ alkylthio, $C_{1-6}$ alkylsulfinyl, phenylsulfinyl, $C_{1-6}$ alkylsulfonyl, phenylsulfonyl, mercapto, sulfino, sulfo, phosphono, sulfamoyl, N-$C_{1-6}$ alkylsulfamoyl, N,N-di-$C_{1-6}$ alkylsulfamoyl, 3- to 6-membered cyclic aminosulfonyl selected from the class consisting of 1-pyrrolidinylsulfonyl, 1-piperidinylsulfonyl, 1-piperazinylsulfonyl, 1-methylpiperazin-4-ylsulfonyl and morpholinosulfonyl, imino, amidino, amino, N-$C_{1-6}$ alkylamino, N,N-di-$C_{1-6}$ alkylamino, 3- to 6-membered cyclic amino selected from the class consisting of 1-azetidinyl, 1-pyrrolidinyl, 1-piperidinyl, 1-piperazinyl, 1-methylpiperazin-4-yl and morpholino, N,N,N-tri-$C_{1-6}$ alkylammonium, $C_{1-6}$ alkanoyl, $C_{1-6}$ alkanoylamino, benzamido, benzoyl, $C_{1-6}$ alkanoyloxy, benzoyloxy, $C_{1-6}$ alkoxy, $C_{2-7}$ alkoxycarbonyl, phenoxy, phenylthio, hydroxy, oxo, thioxo, epoxy, hydroxy-$C_{1-6}$ alkyl, amino-$C_{1-6}$ alkyl, N-$C_{1-6}$ alkylamino-$C_{1-6}$ alkyl, N,N-di-$C_{1-6}$ alkylamino-$C_{1-6}$ alkyl, 3- to 6-membered cyclic amino-$C_{1-6}$ alkyl in which the 3- to 6-membered cyclic amino moiety is selected from the class consisting of 1-azetidinyl, 1-pyrrolidinyl, 1-piperidinyl, 1-piperazinyl, 1-methylpiperazin-4-yl and morpholino, N,N,N-tri-$C_{1-6}$ alkylammonio-$C_{1-6}$ alkyl, carboxyl, carboxy-$C_{1-6}$ alkyl, carbamoyl, N-$C_{1-6}$ alkylcarbamoyl, N,N-di-$C_{1-6}$ alkylcarbamoyl, 3- to 6-membered cyclic aminocarbonyl selected from the class consisting of 1-azetidinylcarbonyl, 1-pyrrolidinylcarbonyl, 1-piperidinylcarbonyl, 1-piperazinylcarbonyl, 1-methylpiperazinl-4-ylcarbonyl and morpholinocarbonyl, cyano, trifluoromethyl or ureido; or a pharmaceutically acceptable salt thereof.

28. A compound according to claim 27 or a salt thereof, wherein $R^1$ stands for an alkyl group having 8 to 20 carbon atoms.

29. A compound according to claim 27 or a salt thereof, wherein $R^1$ stands for an n-octadecyl group.

30. A compound according to claim 27 or a salt thereof, wherein $R^2$ stands for a pyrimidinyl group.

31. A compound according to claim 27 or a salt thereof, wherein $R^3$ stands for a 1-pyridinio group.

32. A compound according to claim 27 or a salt thereof, wherein p denotes 1.

33. A compound according to claim 27 or a salt thereof, wherein q and r denote 2.

* * * * *